US008278460B2

(12) United States Patent
Liu et al.

(10) Patent No.: US 8,278,460 B2
(45) Date of Patent: Oct. 2, 2012

(54) SUBSTITUTED BENZIMIDAZOLES

(75) Inventors: Julie F. Liu, Lexington, MA (US); Scott L. Harbeson, Cambridge, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 12/905,835

(22) Filed: Oct. 15, 2010

(65) Prior Publication Data

US 2011/0172280 A1     Jul. 14, 2011

Related U.S. Application Data

(60) Provisional application No. 61/252,069, filed on Oct. 15, 2009, provisional application No. 61/253,553, filed on Oct. 21, 2009.

(51) Int. Cl.
*A61K 31/4184*     (2006.01)
*C07D 235/08*     (2006.01)
(52) U.S. Cl. ............................ 548/304.4; 514/394
(58) Field of Classification Search ................ None
See application file for complete search history.

(56) References Cited

U.S. PATENT DOCUMENTS

| | | | |
|---|---|---|---|
| 5,360,809 A * | 11/1994 | Axelsson et al. | 514/338 |
| 6,221,335 B1 | 4/2001 | Foster | |
| 6,440,710 B1 | 8/2002 | Keinen et al. | |
| 6,603,008 B1 | 8/2003 | Ando et al. | |
| 7,517,990 B2 | 4/2009 | Ito et al. | |
| 2007/0082929 A1 | 4/2007 | Gant et al. | |
| 2007/0197695 A1 | 8/2007 | Potyen et al. | |
| 2008/0103122 A1 | 5/2008 | Veltri | |

FOREIGN PATENT DOCUMENTS

| | | |
|---|---|---|
| JP | 2009-155300 | 7/2009 |
| WO | WO 95/26325 A2 | 10/1995 |
| WO | WO-96/33191 A1 * | 10/1996 |
| WO | WO-99/19323 A1 * | 4/1999 |
| WO | WO-2004/087690 A2 * | 10/2004 |
| WO | WO 2007/110374 A1 | 10/2007 |
| WO | WO 2007/118651 A1 | 10/2007 |

OTHER PUBLICATIONS

Golub et al., Science, vol. 286, Oct. 15, 1999, pp. 531-537.*
Baillie, T.A., "The Use of Stable Isotopes in Pharmacological Research," *Pharmacological Reviews*, 33(2): 81-132 (1981).
Browne, T.R., "Stable Isotope Techniques in Early Drug Development: An Economic Evaluation," *J. Clin. Pharmacol.*, 38:213-220 (1998).
Cherrah, Y., et al., "Study of Deuterium Isotope Effects on Protein Binding by Gas Chromatography/Mass Spectrometry, Caffeine and Deuterated Isotopomers," *Biomedical and Environmental Mass Spectrometry*, 14:653-657 (1987).
Dyck, L.E., et al., "Effects of Deuterium Substitution on the Catabolism of β-Phenylethylamine: An In Vivo Study," *J. of Neurochemistry*, 46(2):399-404 (1986).

Erichsen, H.K., et al., "A Novel $GABA_A$ Receptor Modulator Attenuates Neuropathic Hypersensitivity in Rat Models of Peripheral Nerve Injury," 12th World Congr Pain, (Aug. 17-22, Glasgow) 2008, Abst PH 244.
Fisher, M.B., et al., "The Complexities Inherent in Attempts to Decrease Drug Clearance by Blocking Sites of CYP-mediated Metabolism," *Current Opinion in Drug Discovery & Development*, 9(1):101-109 (2006).
Foster, A.B., "Deuterium Isotope Effects in Studies of Drug Metabolism," *TIPS*, pp. 524-527 (1984).
Foster, A.B., "Deuterium Isotope Effects in the Metabolism of Drugs and Xenobiotics: Implications for Drug Design," *Advances in Drug Research*, 14:1-40 (1985).
Gouyette, A., "Synthesis of Deuterium-labelled Elliptinium and its Use in Metabolic Studies," *Biomedical and Environmental Mass Spectrometry*, 15:243-247 (1988).
Haskins, N. J., "The Application of Stable Isotopes in Biomedical Research," *Biomedical Mass Spectrometry*, 9(7):269-277 (1982).
Honma, S., et al., "The Metabolism of Roxatidine Acetate Hydrochloride," *Drug Metabolism and Disposition*, 15(4):551-559 (1987).
Kushner, D.J., et al., "Pharmacological Uses and Perspectives of Heavy Water and Deuterated Compounds," *Can. J. Physiol. Pharmacol.*, 77:79-88 (1999).
Mirza, N., et al., "The Subtype Selective $GABA_A$ Receptor Positive Modulator NS11394 Reverses Inflammatory and Neuropathic Pain-Like Behaviours in Animal Models of Injury-Induced Central Sensitazation," 38th *Annual Meeting of the Society for NeuroScience* in Washington, D.C., Nov. 15-19, 2008, Abst 531.26/D27.
Mirza, N., et al., "NS11394 ([3'-[5-(1-hydroxy-1-methyl-ethyl)-benzoimidazol-1-yl]-biphenyl-2-carbonitrile]), a unique subtype-selective $gaba_A$Receptor Positive Modulator: in vitro actions, Pharmacokinetic Properties and in-vivo Anxiolytic Efficacy," 38th *Annual Meeting of the Society for NeuroScience* in Washington, D.C., Nov. 15-19, 2008, Abst 762.2/GG9.
Munro, G., et al., "$GABA_A$ Receptor Subtypes as Novel Targets for Treating Chronic Pain: NS11394 as an Example," *Taking the Pain Out of Drug Discovery 2009, SCI*, London, UK, Mar. 26, 2009.
Munro, G., et al., "Developing Analgesics by Enhancing Spinal Inhibition After Injury: $GABA_A$ Receptor Subtypes as Novel Targets," *TIPS*, 30(9):453-459 (2009).
Park, B.K., et al., "Metabolism of Fluorine-Containing Drugs," *Annu. Rev. Pharmacol. Toxicol.*, 41:443-470 (2001).

(Continued)

*Primary Examiner* — Laura L. Stockton
(74) *Attorney, Agent, or Firm* — Edwards Wildman Palmer LLP; Jeffrey D. Hsi; Mark D. Russett

(57) ABSTRACT

This invention relates to novel substituted benzimidazoles and pharmaceutically acceptable salts thereof. This invention also provides compositions comprising a compound of this invention and the use of such compositions in methods of treating diseases and conditions that are beneficially treated by administering a compound that modulates the $GABA_A$ receptor. This invention also provides novel intermediates for the preparation of the compounds of the invention, and salts thereof.

5 Claims, 1 Drawing Sheet

OTHER PUBLICATIONS

Pieniaszek, H.J., et al., "Moricizine Bioavailability Via Simultaneous, Dual, Stable Isotope Administration: Bioequivalence Implications," *J. Clin. Pharmacol.*, 39:817-825 (1999).

Tonn, G.R., et al., "Simultaneous Analysis of Diphenhydramine and a Stable Isotope Analog ($^2H_{10}$) Diphenhydramine Using Capillary Gas Chromatography with Mass Selective Detection in Biological Fluids from Chronically Instrumented Pregnant Ewes," *Biological Mass Spectrometry*, 22:633-642 (1993).

Wolen, R.L., "The Application of Stable Isotopes to Studies of Drug Bioavailability and Bioequivalence," *J. Clin. Pharmacol.*, 26:419-424 (1986).

Notification of Transmittal of the International Search Report and the Written Opinion of the International Search Authority, or the Declaration, International Application No. PCT/US2010/052915; Date of Mailing: Jan. 12, 2011.

* cited by examiner

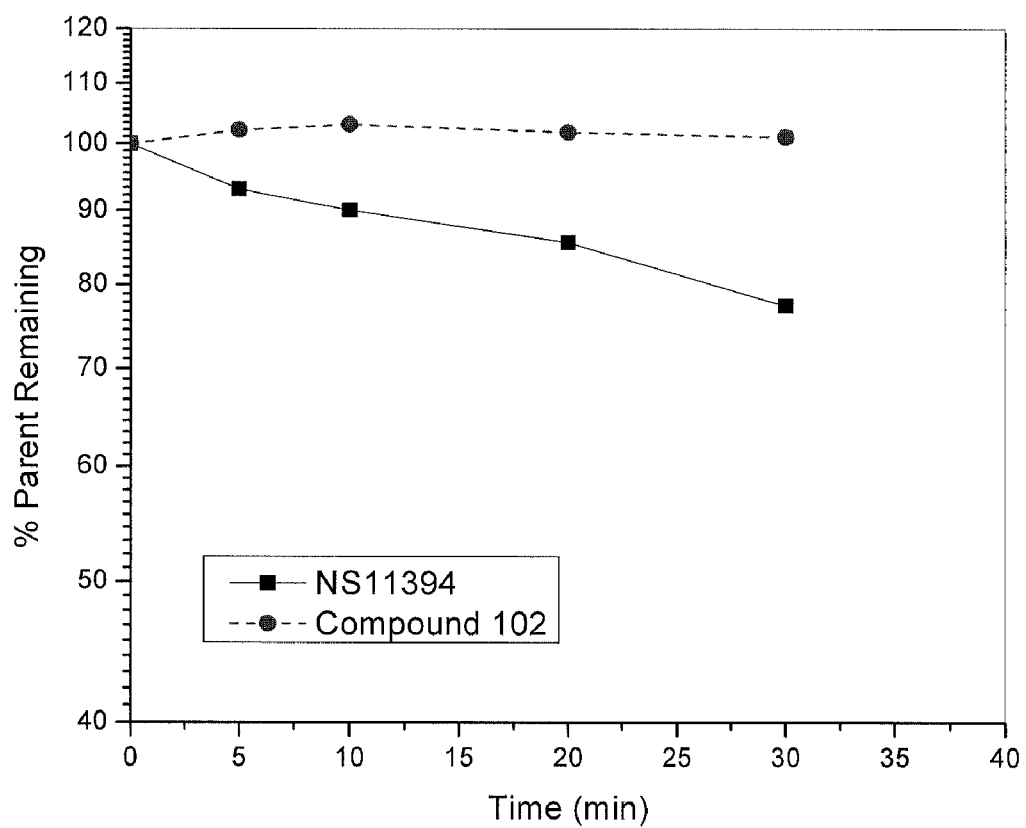

SUBSTITUTED BENZIMIDAZOLES

RELATED APPLICATIONS

This application claims the benefit of U.S. Provisional Application No. 61/252,069, filed on Oct. 15, 2009 and U.S. Provisional Application No. 61/253,553, filed on Oct. 21, 2009. The entire teachings of the above applications are incorporated herein by reference.

BACKGROUND OF THE INVENTION

Many current medicines suffer from poor absorption, distribution, metabolism and/or excretion (ADME) properties that prevent their wider use. Poor ADME properties are also a major reason for the failure of drug candidates in clinical trials. While formulation technologies and prodrug strategies can be employed in some cases to improve certain ADME properties, these approaches fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment.

In some select cases, a metabolic inhibitor will be co-administered with a drug that is cleared too rapidly. Such is the case with the protease inhibitor class of drugs that are used to treat HIV infection. These drugs are typically co-dosed with ritonavir, an inhibitor of cytochrome P450 enzyme 3A4 (CYP3A4), the enzyme typically responsible for their metabolism. Ritonavir causes adverse effects and adds to the pill burden for HIV patients who must already take a combination of different drugs. Similarly, quinidine has been added to dextromethorphan for the purpose of reducing rapid CYP2D6 metabolism in a treatment of pseudobulbar affect. Quinidine, however, is a CYP2D6 inhibitor that has unwanted side effects that greatly limit its use in potential combination therapy.

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. This can cause those other drugs to accumulate in the body to toxic levels.

A potentially attractive strategy for improving a drug's metabolic properties is deuterium modification. In this approach, one attempts to slow the CYP-mediated metabolism of a drug by replacing one or more hydrogen atoms with deuterium atoms. Deuterium is a safe, stable, non-radioactive isotope of hydrogen. Deuterium forms stronger bonds with carbon than hydrogen does. In select cases, the increased bond strength imparted by deuterium can positively impact the ADME properties of a drug, creating the potential for improved drug efficacy, safety, and tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al., J Pharm Sci, 1975, 64:367-91; Foster, A B, Adv Drug Res, 1985, 14:1-40 ("Foster"); Kushner, D J et al., Can J Physiol Pharmacol, 1999, 79-88; Fisher, M B et al., Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism. (See Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its undeuterated counterpart. See, for example, Fukuto et al. (J. Med. Chem. 1991, 34, 2871-76). Many drugs have multiple sites where metabolism is possible. The site(s) where deuterium substitution is required and the extent of deuteration necessary to see an effect on metabolism, if any, will be different for each drug.

$GABA_A$ receptors are ligand-gated chloride channels that mediate the inhibitory effects of γ-aminobutyric acid (GABA) in the central nervous system. $GABA_A$ receptors are heteromeric proteins of five subunits primarily found as receptors containing α, β, and γ subunits in a 2:2:1 stoichiometry. $GABA_A$ receptors containing the α1, α2, α3, or α5 subunits contain a binding site for benzodiazepines, which is the basis for the pharmacologic activity of benzodiazepines.

NS11394, also known as 3'-[5-(1-hydroxy-1-methyl-ethyl)-1H-benzimidazol-1-yl]biphenyl-2-carbonitrile, is a $GABA_A$ receptor modulator. NS11394 has been found to completely reverse inflammatory and neuropathic pain-like behaviors in animal models following oral administration and is well tolerated (Mirza, N. et al., 38th annual meeting of the Society for NeuroScience in Washington D.C., Nov. 15-19, 2008, Abst 531.26). It has also been shown that NS11394 is potent and highly effective in rodent anxiety models, and that the compound's anxiolytic efficacy is most likely mediated through its high efficacy at $GABA_A$ α3 receptors (Mirza, N. et al., 38th annual meeting of the Society for NeuroScience in Washington D.C., Nov. 15-19, 2008, Abst 762.2). Similar results have been presented by Munro, G. et al. at the Taking the Pain Out of Drug Discovery 2009 Meeting in London, UK (Mar. 26, 2009) and by Erichsen, H. K. et al., $12^{th}$ World Congr Pain (Aug. 17-22, Glasgow) 2008, Abst PH 244. No dependence issues were observed in this study.

The GABA subtype selectivity for NS11394 is in the order α5>α3>α2>α1. Indications for which NS 11394 is useful include anxiety disorders, such as panic disorder with or without agoraphobia, agoraphobia without history of panic disorder, animal and other phobias including social phobias, obsessive-compulsive disorder, and generalized or substance-induced anxiety disorder; stress disorders including post-traumatic and acute stress disorder; sleep disorders; memory disorder; neuroses; convulsive disorders, for example epilepsy, seizures, convulsions, or febrile convulsions in children; migraine; mood disorders; depressive or bipolar disorders, for example depression, single-episode or recurrent major depressive disorder, dysthymic disorder, bipolar disorder, bipolar I and bipolar II manic disorders, and cyclothymic disorder; psychotic disorders, including schizophrenia; neurodegeneration arising from cerebral ischemia; attention deficit hyperactivity disorder; pain and nociception, e.g. neuropathic pain and inflammatory pain; emesis, including acute, delayed and anticipatory emesis, in particular emesis induced by chemotherapy or radiation; motion sickness, post-operative nausea and vomiting; eating disorders including anorexia nervosa and bulimia nervosa; premenstrual syndrome; neuralgia, e.g. trigeminal neuralgia; muscle spasm or spasticity, e.g. in paraplegic patients; the effects of substance abuse or dependency, including alcohol withdrawal; cognitive disorders, such as Alzheimer's disease; cerebral ischemia, stroke, head trauma; tinnitus; disorders of circadian rhythm, e.g. in subjects suffering from the effects of jet lag or shift work; diabetes, type 1 diabetes (insulin-dependent diabetes mellitus), type 2 diabetes, hyperinsulinemia; and other inflammatory diseases and auto immune disorders. Other indications are described in patent publication WO 2007110374.

Despite the purported beneficial activities of NS11394, there is a continuing need for new compounds that have beneficial effects as anxiolytics and antinociceptives without sedative and proconvulsant effects.

SUMMARY OF THE INVENTION

This invention relates to novel deuterated benzimidazoles and pharmaceutically acceptable salts thereof. This invention also provides compositions comprising a compound of this invention and the use of such compositions in methods of treating diseases and conditions that are beneficially treated by administering a $GABA_A$ receptor modulator.

BRIEF DESCRIPTION OF THE DRAWING

The FIGURE shows a plot of percent of compound remaining over time for NS-11394 and Compound 102.

DEFINITIONS

The term "treat" means decrease, suppress, attenuate, diminish, arrest, or stabilize the development or progression of a disease (e.g., a disease or disorder delineated herein).

"Disease" means any condition or disorder that damages or interferes with the normal function of a cell, tissue, or organ.

The term "alkyl" refers to a monovalent saturated hydrocarbon group. $C_1$-$C_6$ alkyl is an alkyl having from 1 to 6 carbon atoms. An alkyl may be linear or branched. Examples of alkyl groups include methyl; ethyl; propyl, including n-propyl and isopropyl; butyl, including n-butyl, isobutyl, sec-butyl, and t-butyl; pentyl, including, for example, n-pentyl, isopentyl, and neopentyl; and hexyl, including, for example, n-hexyl and 2-methylpentyl.

The term "aryl" refers to a monovalent aromatic carbocyclic ring system, which may be a monocyclic, fused bicyclic, or fused tricyclic ring system. The term "$C_6$-$C_{14}$ aryl" refers to an aryl having from 6 to 14 ring carbon atoms. An example of $C_6$-$C_{14}$ aryl is $C_6$-$C_{10}$ aryl. More particular examples of aryl groups include phenyl, naphthyl, anthracyl, and phenanthryl.

The term "heteroaryl" refers to a monovalent aromatic ring system wherein from 1 to 4 ring atoms are heteroatoms independently selected from the group consisting of O, N and S, and having from 5 to 14 ring atoms. The ring system may be a monocyclic, fused bicyclic, or fused tricyclic ring system. The term "5 to 14-membered heteroaryl" refers to a heteroaryl wherein the number of ring atoms is from 5 to 14. Examples of 5 to 14-membered heteroaryl include 5 to 10-membered heteroaryl and 5 to 6-membered heteroaryl. More particular examples of heteroaryl groups include furanyl, furazanyl, imidazolinyl, isothiazolyl, isoxazolyl, oxadiazolyl, oxazolyl, pyrimidinyl, phenanthridinyl, pyrazinyl, pyrazolinyl, pyrazolyl, pyridazinyl, pyridooxazolyl, pyridoimidazolyl, pyridothiazolyl, pyridinyl, pyrimidinyl, pyrrolinyl, thiadiazinyl, thiadiazolyl, thienyl, thienothiazolyl, thienooxazolyl, thienoimidazolyl, thiophenyl, triazinyl, and triazolyl.

Unless otherwise specified, all atoms in each alkyl, aryl or heteroaryl are present at their natural isotopic abundance.

It will be recognized that some variation of natural isotopic abundance occurs in a synthesized compound depending upon the origin of chemical materials used in the synthesis. Thus, a preparation of NS11394 will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species that differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The invention also provides salts of the compounds of the invention.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any salt that is non-toxic upon administration to a recipient at a therapeutically effective dose level, and is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free of another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes specified herein (e.g., formulation into therapeutic products, intermediates for use in production of therapeutic compounds, isolatable or storable intermediate compounds, treating a disease or condition responsive to therapeutic agents).

"D" refers to deuterium. "Stereoisomer" refers to both enantiomers and diastereomers. "Tert" and "t-" each refer to tertiary. "US" refers to the United States of America.

The phrase "substituted with deuterium" means that one or more hydrogen atoms in the indicated moiety are replaced with an equal number of deuterium atoms, wherein each deuterium atom is present at an abundance that is at least 3340 times greater than the natural abundance of deuterium.

The term "deuteroalkyl" refers to an alkyl substituted with deuterium.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present invention provides a compound of Formula I:

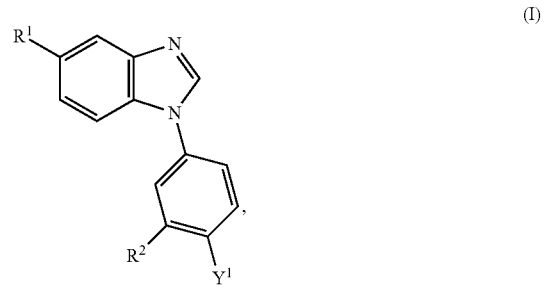

(I)

or a pharmaceutically acceptable salt thereof, wherein:
$R^1$ is
(a) $C_1$-$C_6$ alkyl or $C_1$-$C_6$ deuteroalkyl;
(b) —$OC_1$-$C_6$ alkyl or —$OC_1$-$C_6$ deuteroalkyl;
(c) —C(O)H;
(d) —C(O)$C_1$-$C_6$ alkyl or —C(O)$C_1$-$C_6$ deuteroalkyl;
(e) —C(O)O$C_1$-$C_6$ alkyl or —C(O)O$C_1$-$C_6$ deuteroalkyl;
(f) —$CR^3$=$NOR^4$;

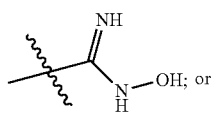

(g)

; or

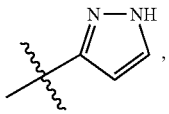

wherein the alkyl or deuteroalkyl portion of R¹ in (a), (b) or (d) is optionally substituted with one to five groups independently selected from —F, —Cl, —Br, and —OH;

and wherein (h) is optionally substituted with one or more deuterium;

R² is aryl or heteroaryl, wherein R² is optionally substituted with one or two groups independently selected from the group consisting of —F, —Cl, —Br, —OCH₃, —OCD₃, —CH₂OH, —CD₂OH, —CH₃, —CD₃, —CH₂CH₃, —CD₂CH₃, —CH₂CD₃, —CD₂CD₃, —CF₃, —CN, —C(O)H, —C(O)OCH₃, —NH₂, —C(O)CH₃, —SC(O)CD₃, —SCH₃, —SCD₃, —S(O)CH₃, —S(O)CD₃, —S(O₂)CH₃, —S(O₂)CD₃, and —CH═NOH;

R³ is selected from hydrogen, deuterium, C₁-C₆ alkyl, and C₁-C₆ deuteroalkyl;

R⁴ is C₁-C₆ alkyl or C₁-C₆ deuteroalkyl, wherein R⁴ is optionally substituted with one or more groups independently selected from —OH, —N(C₁-C₆ alkyl)₂, —N(C₁-C₆ deuteroalkyl)₂ and —N(C₁-C₆ alkyl)(C₁-C₆ deuteroalkyl); and Y¹ is hydrogen, deuterium, —Cl, or —F;

with the proviso that at least one of R¹ and R² comprises deuterium.

In one embodiment, R² is 3-pyridyl.

In one embodiment, R¹ is C₁-C₄ alkyl or C₁-C₄ deuteroalkyl, wherein R¹ is optionally substituted as defined in Formula I.

In one embodiment, R¹ is

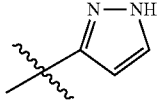

optionally substituted with deuterium; C₁-C₄ alkyl optionally substituted with one or more groups independently selected from —F and —OH; or C₁-C₄ deuteroalkyl optionally substituted with one or more groups independently selected from —F and —OH; and R² is phenyl or pyridyl each optionally substituted as defined in Formula I. In one aspect of this embodiment, R² is 3-pyridyl optionally substituted as defined in Formula I. In one aspect of this embodiment, R¹ is

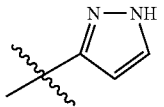

optionally substituted with deuterium; —CF₃; —C(CH₃)₃; —C(CD₃)₃; —CH(OH)CH₃; —CH(OH)CD₃; —CD(OH)CH₃; —CD(OH)CD₃; —C(OH)(CH₃)₂; —C(OH)(CD₃)₂; or —C(OH)(CH₃)CD₃ and R² is (a) phenyl optionally substituted with one or two groups independently selected from —OCH₃, —OCD₃, —CH₃, —CD₃, —CN, —Cl and —F; or (b) pyridyl optionally substituted with one or two groups independently selected from —CH₃, —CD₃, —CN, and —F.

In a specific aspect of this embodiment, (b) is 3-pyridyl optionally substituted with one or two groups independently selected from —CH₃, —CD₃, —CN, and —F.

In one embodiment, R¹ is selected from —CH₃, —CD₃, —CF₃, —CH₂F, —CHF₂, —CD₂F, CDF₂, —CF₂CH₃, —CF₂CD₃, —CF(CH₃)₂, —CF(CD₃)₂, —CH₂OH, —CD₂OH, —C(OH)(CH₃)₂, —C(OH)(CD₃)₂, —CH(OH)CH₃, —CD(OH)CH₃, —CH(OH)CD₃, —CD(OH)CD₃, —(R)CD(OH)CH₃, —(R)CH(OH)CD₃, —(R)CD(OH)CD₃, —(S)CD(OH)CH₃, —(S)CH(OH)CD₃, —(S)CD(OH)CD₃, —C(CH₃)₃, —C(CD₃)₃, —OCH₃, —OCD₃, —C(O)H, —C(O)CH₃, —C(O)CD₃, —COOCH₃, —COOCD₃,

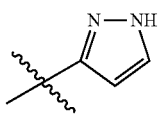

optionally substituted with deuterium, and —CR³═NOR⁴ where R³ and R⁴ are as defined in Formula I. Specific examples of R¹ include —CH₃, —CD₃, —CF₃, —CF₂CH₃, —CF₂CD₃, —CF(CH₃)₂, —CF(CD₃)₂, —C(OH)(CH₃)₂, —C(OH)(CD₃)₂, —CD(OH)CH₃, —CH(OH)CD₃, —CD(OH)CD₃, —(R)CD(OH)CH₃, —(R)CH(OH)CD₃, —(R)CD(OH)CD₃, —(S)CD(OH)CH₃, —(S)CH(OH)CD₃, —(S)CD(OH)CD₃, —C(CH₃)₃, and —C(CD₃)₃.

In one embodiment, R² is selected from phenyl, pyridazinyl, pyrimidinyl, pyrazinyl, furyl, pyrrolyl, pyrazolyl, oxazolyl, isoxazolyl, imidazolyl, oxadiazolyl, thiadiazolyl, triazolyl, tetrazolyl, pyridyl, thienyl, and thiazolyl, wherein R² is optionally substituted with one or two groups independently selected from the group consisting of —F, —OCH₃, —OCD₃, —CH₂OH, —CD₂OH, —CH₃, —CD₃, —CH₂CH₃, —CD₂CH₃, —CH₂CD₃, —CD₂CD₃, —Cl, —CF₃, —CN, —C(O)H, —C(O)OCH₃, —NH₂, —C(O)CH₃, —C(O)CD₃, —SCH₃, —SCD₃, —S(O)CH₃, —S(O)CD₃, and —CH═NOH. Examples of R² include phenyl, pyridyl, such as 2- and 3-pyridyl, thienyl, or thiazolyl, wherein R² is optionally substituted with one or two groups independently selected from —F, —Cl, —OCH₃, —OCD₃, —CH₃, —CD₃, —CH₂CH₃, —CD₂CH₃, —CH₂CD₃, —CD₂CD₃, —CF₃, —CN, and —C(O)H.

In one embodiment, R³ is selected from hydrogen, deuterium, —CH₃, and —CD₃.

In one embodiment, R⁴ is selected from —CH₃, —CD₃, —CH₂CH₃, —CD₂CH₃, —CH₂CD₃, —CD₂CD₃, CH(OH)CH₃, —CD(OH)CH₃, —CH(OH)CD₃, —CD(OH)CD₃, —CH₂CH₂N(CH₃)₂, —CD₂CH₂N(CH₃)₂, —CH₂CD₂N(CH₃)₂, —CD₂CD₂N(CH₃)₂, —CH₂CH₂N(CD₃)₂, —CD₂CH₂N(CD₃)₂, —CH₂CD₂N(CD₃)₂, and —CD₂CD₂N(CD₃)₂.

In one embodiment, R² is phenyl, pyridyl, such as 2- and 3-pyridyl, thienyl, or thiazolyl, wherein R² is optionally substituted with one or two groups independently selected from —F, —Cl, —OCH₃, —OCD₃, —CH₃, —CD₃, —CH₂CH₃, —CD₂CH₃, —CH₂CD₃, —CD₂CD₃, —CF₃, —CN, and —C(O)H; R³ is selected from hydrogen, deuterium, —CH₃, and —CD₃; and R⁴ is selected from —CH₃, —CD₃, —CH₂CH₃, —CD₂CH₃, —CH₂CD₃, —CD₂CD₃, CH(OH)CH₃, —CD(OH)CH₃, —CH(OH)CD₃, —CD(OH)CD₃, —CH₂CH₂N(CH₃)₂, —CD₂CH₂N(CH₃)₂, —CH₂CD₂N(CH₃)₂, —CD₂CD₂N(CH₃)₂, —CH₂CH₂N(CD₃)₂, —CD₂CH₂N(CD₃)₂, —CH₂CD₂N(CD₃)₂, and —CD₂CD₂N(CD₃)₂.

In one embodiment, $Y^1$ is hydrogen or —F. In an example of this embodiment, $R^1$ is selected from —CH$_3$, —CD$_3$, —CF$_3$, —CF$_2$CH$_3$, —CF$_2$CD$_3$, —CF(CH$_3$)$_2$, —CF(CD$_3$)$_2$, —C(OH)(CH$_3$)$_2$, —C(OH)(CD$_3$)$_2$, —C(CH$_3$)$_3$, and —C(CD$_3$)$_3$; and $R^2$ is phenyl, pyridyl, thienyl, or thiazolyl wherein $R^2$ is optionally substituted with one or two groups independently selected from —F, —Cl, —OCH$_3$, —OCD$_3$, —CH$_3$, —CD$_3$, —CH$_2$CH$_3$, —CD$_2$CH$_3$, —CH$_2$CD$_3$, —CD$_2$CD$_3$, —CF$_3$, —CN, and —C(O)H.

In one embodiment, $R^1$ is

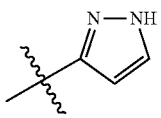

optionally substituted with deuterium; —CF$_3$, —C(CH$_3$)$_3$, —C(CD$_3$)$_3$, —CH(OH)CH$_3$, —CH(OH)CD$_3$, —CD(OH)CH$_3$, —CD(OH)CD$_3$, —C(OH)(CH$_3$)$_2$, —C(OH)(CD$_3$)$_2$, or —C(OH)(CH$_3$)CD$_3$, and $R^2$ is 2-cyanophenyl, 2-methoxyphenyl, 2-trideuteromethoxyphenyl, or 2-fluoro-3-pyridyl, wherein the phenyl ring of $R^2$ is optionally substituted with one or more fluorine and optionally substituted with one or more chlorine.

In another embodiment, $R^2$ is:

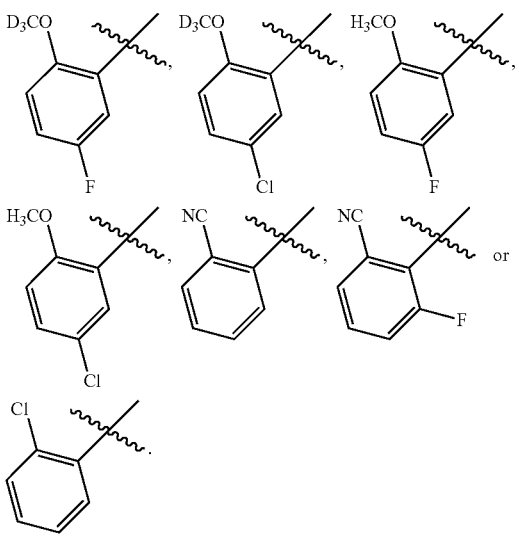

In one aspect of this embodiment, $R^1$ is

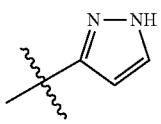

optionally substituted with deuterium; C$_1$-C$_4$ alkyl optionally substituted with one or more groups independently selected from —F and —OH; or C$_1$-C$_4$ deuteroalkyl optionally substituted with one or more groups independently selected from —F and —OH. In an example of this aspect, $R^1$ is

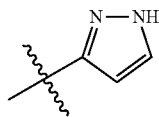

optionally substituted with deuterium; —CF$_3$; —C(CH$_3$)$_3$; —C(CD$_3$)$_3$; —CH(OH)CH$_3$; —CH(OH)CD$_3$; —CD(OH)CH$_3$; —CD(OH)CD$_3$; —C(OH)(CH$_3$)$_2$; —C(OH)(CD$_3$)$_2$; or —C(OH)(CH$_3$)CD$_3$.

In yet another embodiment, $R^2$ is pyridyl optionally substituted with one or two groups independently selected from —CH$_3$, —CD$_3$, —CN, and —F. In one aspect of this embodiment, $R^1$ is

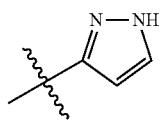

optionally substituted with deuterium; C$_1$-C$_4$ alkyl optionally substituted with one or more groups independently selected from —F and —OH; or C$_1$-C$_4$ deuteroalkyl optionally substituted with one or more groups independently selected from —F and —OH. In example of this aspect, $R^1$ is

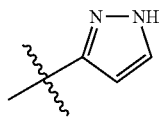

optionally substituted with deuterium; —CF$_3$; —C(CH$_3$)$_3$; —C(CD$_3$)$_3$; —CH(OH)CH$_3$; —CH(OH)CD$_3$; —CD(OH)CH$_3$; —CD(OH)CD$_3$; —C(OH)(CH$_3$)$_2$; —C(OH)(CD$_3$)$_2$; or —C(OH)(CH$_3$)CD$_3$.

In another embodiment, $R^2$ is pyridyl optionally substituted with one or two groups independently selected from —CH$_3$, —CD$_3$, —CN, and —F wherein the pyridyl nitrogen is ortho or meta relative to the point of attachment of $R^2$ to the benzimidazolyl of Formula I. In one aspect of this embodiment, $R^1$ is

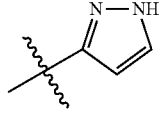

optionally substituted with deuterium; C$_1$-C$_4$ alkyl optionally substituted with one or more groups independently selected from —F and —OH; or C$_1$-C$_4$ deuteroalkyl optionally substituted with one or more groups independently selected from —F and —OH. In an example of this aspect, $R^1$ is

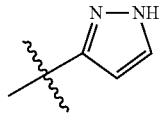

optionally substituted with deuterium; —CF₃; —C(CH₃)₃; —C(CD₃)₃; —CH(OH)CH₃; —CH(OH)CD₃; —CD(OH)CH₃; —CD(OH)CD₃; —C(OH)(CH₃)₂; —C(OH)(CD₃)₂; or —C(OH)(CH₃)CD₃.

In yet another embodiment, R² is selected from:

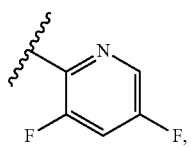 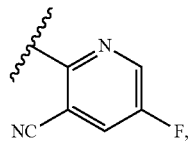

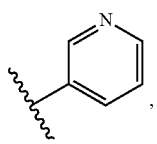 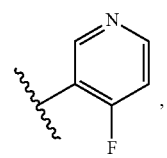

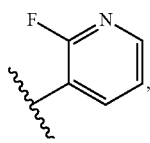 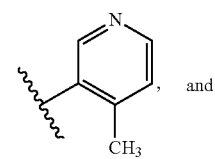 and

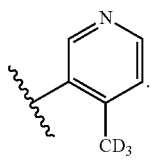

In one aspect of this embodiment, R¹ is

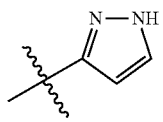

optionally substituted with deuterium; C₁-C₄ alkyl optionally substituted with one or more groups independently selected from —F and —OH; or C₁-C₄ deuteroalkyl optionally substituted with one or more groups independently selected from —F and —OH. In an example of this aspect, R¹ is

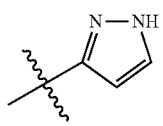

optionally substituted with deuterium; —CF₃; —C(CH₃)₃; —C(CD₃)₃; —CH(OH)CH₃; —CH(OH)CD₃; —CD(OH)CH₃; —CD(OH)CD₃; —C(OH)(CH₃)₂; —C(OH)(CD₃)₂; or —C(OH)(CH₃)CD₃.

In one embodiment of this invention the compound of Formula I is a compound of Formula Ia:

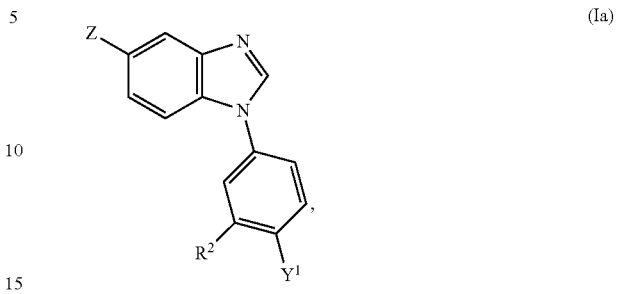

(Ia)

or a pharmaceutically acceptable salt thereof, wherein:
R² is defined as in Formula I;
Z is —C(CH₃)₃, —C(CD₃)₃, —CH(OH)CH₃, —CH(OH)CD₃, —CD(OH)CH₃, —CD(OH)CD₃, —C(OH)(CH₃)₂, —C(OH)(CD₃)₂, or —C(OH)(CH₃)CD₃; and
Y¹ is hydrogen or —F;
with the proviso that if Z does not comprise deuterium; then R² comprises deuterium.

One embodiment provides compounds of Formula Ia, wherein R² is:

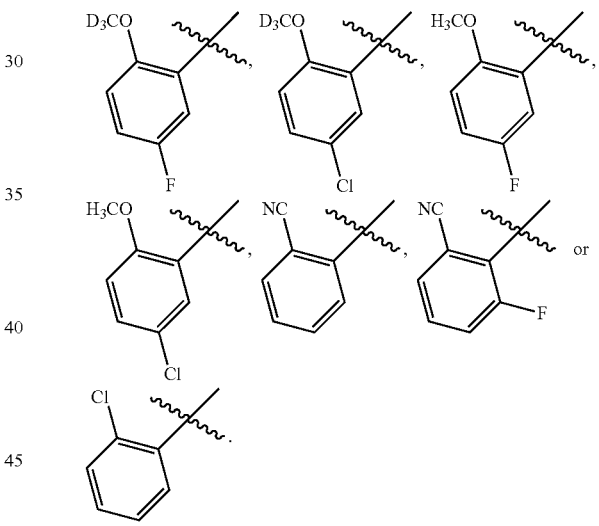

One embodiment of this invention provides a compound of Formula Ia, wherein Z is —C(CH₃)₃ or —C(CD₃)₃. In one aspect of this embodiment, Y¹ is hydrogen. In another aspect, Y¹ is —F.

One embodiment provides compounds of Formula Ia, wherein Z is —C(OH)(CD₃)₂. In one aspect of this embodiment, Y¹ is hydrogen. In another aspect, Y¹ is —F.

One embodiment provides compounds of Formula Ia, wherein Z is —C(OH)(CH₃)₂. In one aspect of this embodiment, Y¹ is hydrogen. In another aspect, Y¹ is —F.

One embodiment provides a compound of Formula Ia, wherein Z is —CH(OH)(CH₃). In one aspect of this embodiment, Y¹ is hydrogen. In another aspect, Y¹ is —F.

One embodiment provides a compound of Formula Ia, wherein Z is —CD(OH)(CH₃). In one aspect of this embodiment, Y¹ is hydrogen. In another aspect, Y¹ is —F.

One embodiment provides a compound of Formula Ia, wherein Z is —CH(OH)(CD₃). In one aspect of this embodiment, Y¹ is hydrogen. In another aspect, Y¹ is —F.

One embodiment provides a compound of Formula Ia, wherein Z is —CD(OH)(CD₃). In one aspect of this embodiment, Y¹ is hydrogen. In another aspect, Y¹ is —F.

One embodiment of the invention provides a compound of Formula Ia wherein Z is —C(CH₃)₃, —C(CD₃)₃, —C(OH)(CH₃)₂, —C(OH)(CD₃)₂, —CH(OH)(CH₃), —CD(OH)(CH₃), —CH(OH)(CD₃), or —CD(OH)(CD₃). In one aspect of this embodiment, Z is —C(CD₃)₃ or —C(OH)(CD₃)₂. In one aspect of this embodiment Z is —C(CD₃)₃. In another aspect, Z is —C(OH)(CD₃)₂. In another aspect of this embodiment, R² is phenyl or pyridyl, wherein R² is optionally substituted as defined in Formula Ia. In one aspect of this embodiment, Y¹ is hydrogen. In another aspect, Y¹ is —F.

One embodiment provides a compound of Formula Ia wherein R² is phenyl or pyridyl, wherein R² is optionally substituted as defined in Formula Ia. In one aspect of this embodiment, Y¹ is hydrogen. In another aspect, Y¹ is —F. In one aspect of this embodiment, R² is phenyl optionally substituted with one or two groups independently selected from —CH₃, —CD₃, —CN, —OCH₃, —OCD₃, —Cl and —F. In a more specific aspect, R² is phenyl optionally substituted with one or two groups independently selected from —CN, —OCH₃, —OCD₃, —Cl and —F. In an even more specific aspect, R² is:

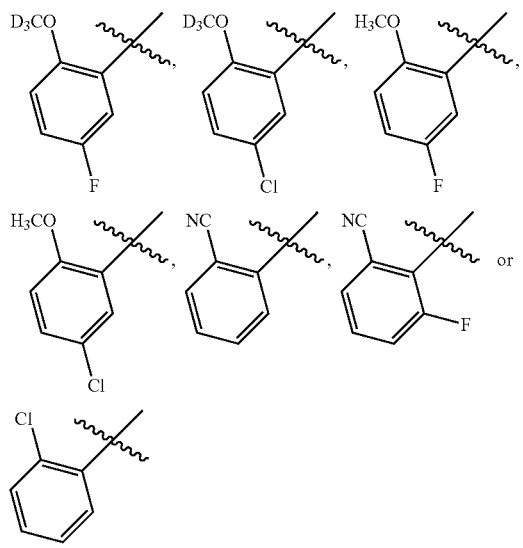

One embodiment provides a compound of Formula Ia, wherein R² is pyridyl optionally substituted as defined in Formula Ia, In one aspect of this embodiment, R² is pyridyl optionally substituted with one or two groups independently selected from —CH₃, —CD₃, —CN, and —F. In a more specific example of this aspect, the pyridyl nitrogen is ortho or meta relative to the point of attachment of R² to the benzimidazolyl of Formula Ia. In a more specific aspect, R² is:

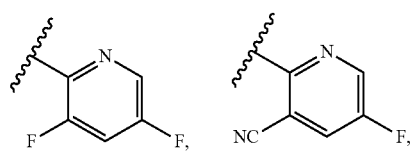

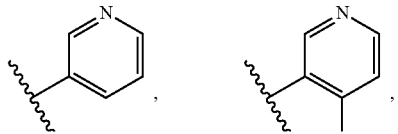

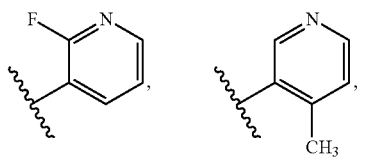

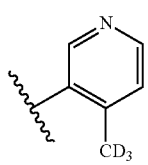

In one embodiment of the compound of Formula Ia, Y¹ is hydrogen. In another embodiment of the compound of Formula Ia, Y¹ is —F.

In one embodiment of the compound of Formula Ia,

R² is defined as in Formula I;

Z is —C(CH₃)₃, —C(CD₃)₃, —C(OH)(CH₃)₂, —C(OH)(CD₃)₂, or —C(OH)(CH₃)CD₃; and

Y¹ is hydrogen or —F;

with the proviso that if Z does not comprise deuterium; then R² comprises deuterium. In one aspect of this embodiment, Z is —C(CH₃)₃, —C(CD₃)₃, —C(OH)(CH₃)₂, or —C(OH)(CD₃)₂.

In one embodiment of the compound of Formula Ia,

R² is defined as in Formula I;

Z is —CH(OH)(CH₃), —CD(OH)(CH₃), —CH(OH)(CD₃), or —CD(OH)(CD₃); and

Y¹ is hydrogen or —F;

with the proviso that if Z does not comprise deuterium; then R² comprises deuterium. In one aspect of this embodiment, the compound of Formula Ia is a mixture of (R) and (S) stereoisomers at C₁ of the Z—CH(OH)(CH₃), —CD(OH)(CH₃), —CH(OH)(CD₃), or —CD(OH)(CD₃) group. In another aspect of this embodiment, C₁ of the Z—CH(OH)(CH₃), —CD(OH)(CH₃), —CH(OH)(CD₃), or —CD(OH)(CD₃) group has the (R) stereochemistry. In yet another aspect of this embodiment, C₁ of the Z—CH(OH)(CH₃), —CD(OH)(CH₃), —CH(OH)(CD₃), or —CD(OH)(CD₃) group has the (S) stereochemistry.

Specific examples of a compound of Formula I or Ia include the compounds in Table 1 below.

TABLE 1
Examples of Specific Compounds of Formula I or Ia
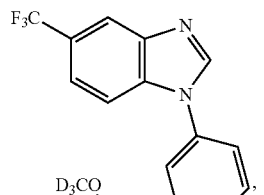
100
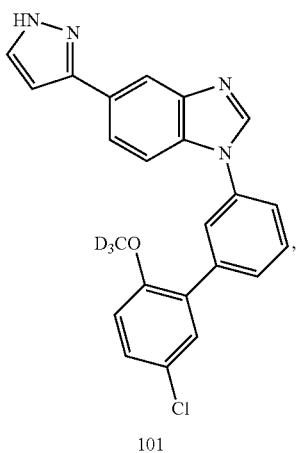
101
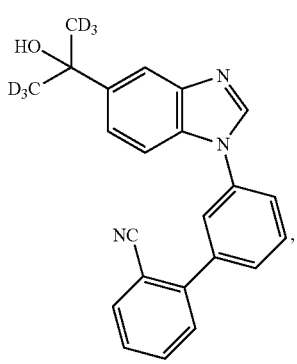
102
TABLE 1-continued
Examples of Specific Compounds of Formula I or Ia
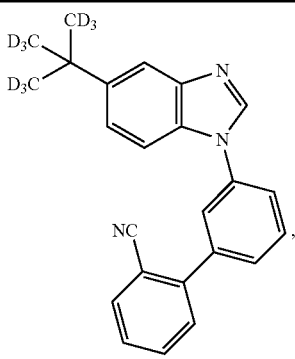
103
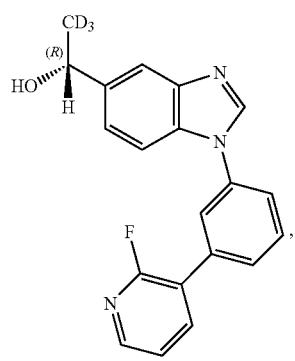
104
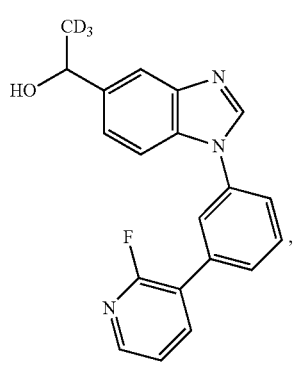
105
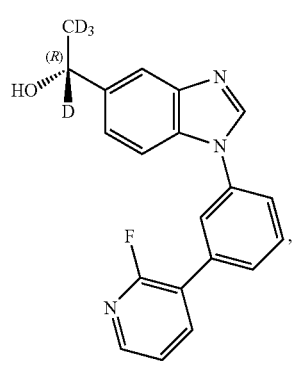
106

TABLE 1-continued

Examples of Specific Compounds of Formula I or Ia

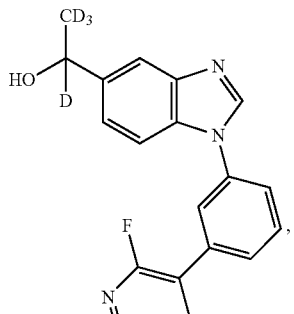
107

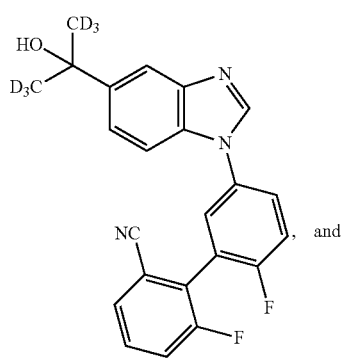
108

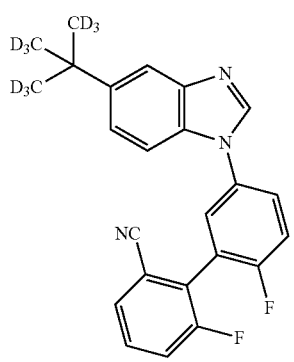
109 or a pharmaceutically acceptable salt of any of the foregoing.

Compounds of this invention include also the specific examples shown below.

110

111

112 or pharmaceutically acceptable salts thereof.

A useful intermediate 10, wherein $Y^1$ is as defined in Formula I, $R^6$ is selected from $R^1$, —CN, and —(O)NH$_2$ and X is selected from —Cl, —Br and —I, is described herein and can be used to prepare compounds of Formula I or Ia.

10

Known examples of intermediate 10 include, but are not limited to, the following:
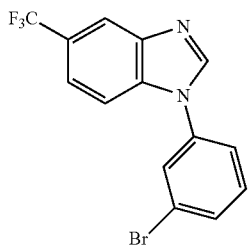
10a
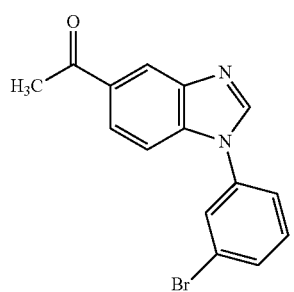
10b
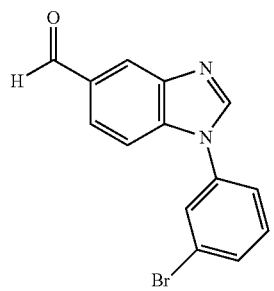
10c
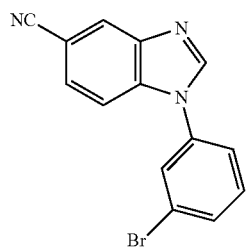
10d
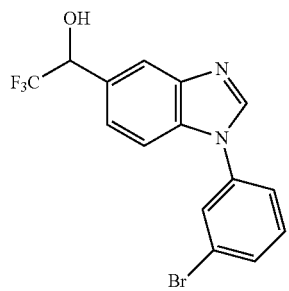
10e
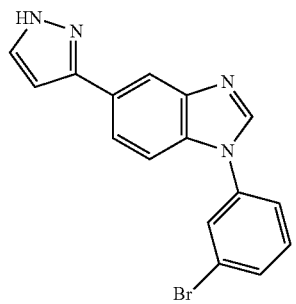
10f
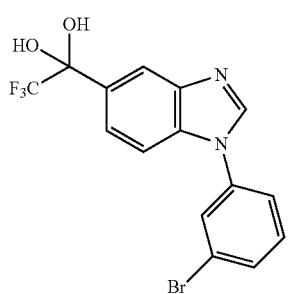
10g
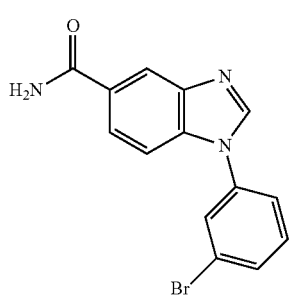
10h
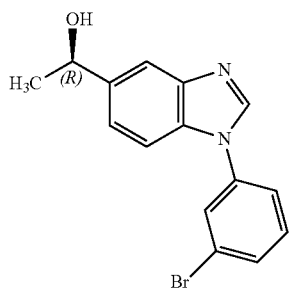
10i
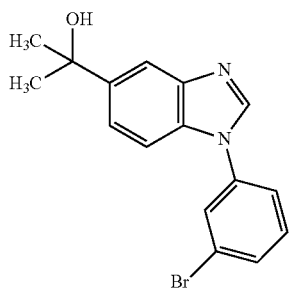
10j

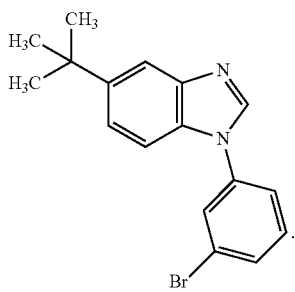

10r

These known intermediates 10a-10j and 10r may be prepared as described in EP 563001, WO 96/33194, WO 96/33191, WO 07/110,374, EP 616807 and U.S. Pat. No. 5,554,630.

In addition, novel deuterated intermediates 10 include compounds of Formula II or salts thereof

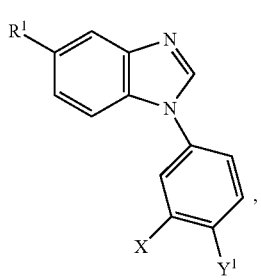

(II)

wherein $R^1$ and $Y^1$ are defined as in Formula I and X is selected from —Cl, —Br and —I, with the proviso that $R^1$ comprises deuterium.

Examples of Formula II include, but are not limited to, the following:

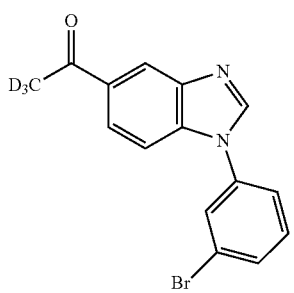

10k

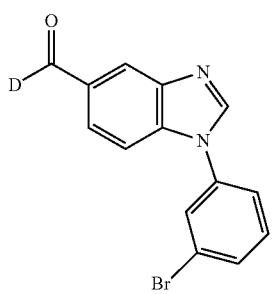

10m

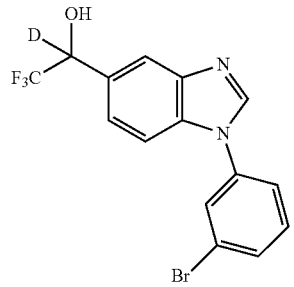

10n

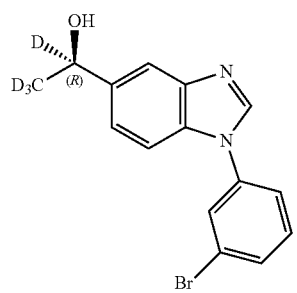

10p

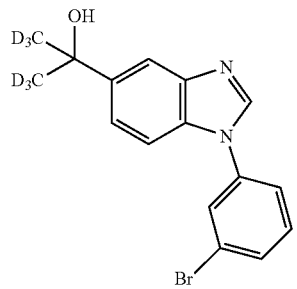

10q

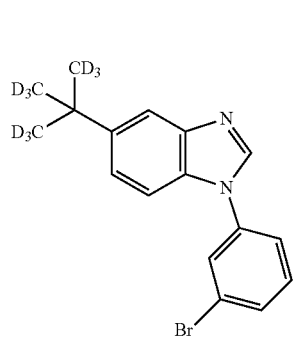

10s

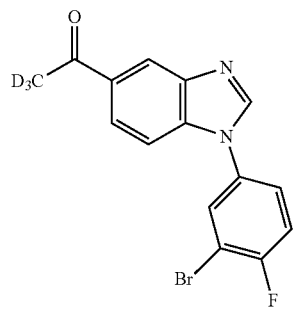

10t

-continued

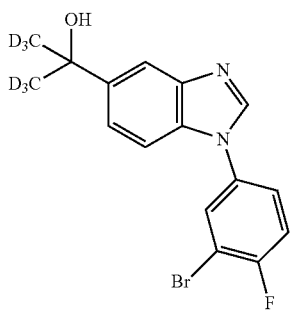
10u

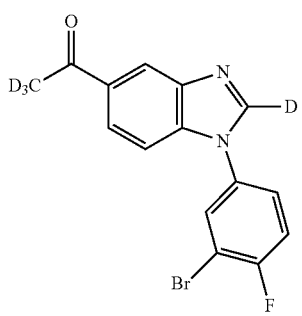
10x

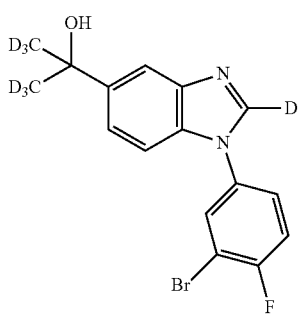
10y

Novel intermediates also include compounds 10v and 10w:

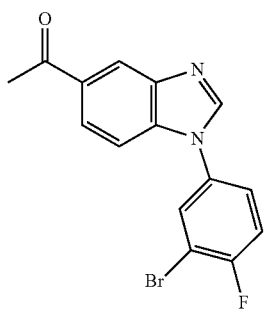
10v

-continued

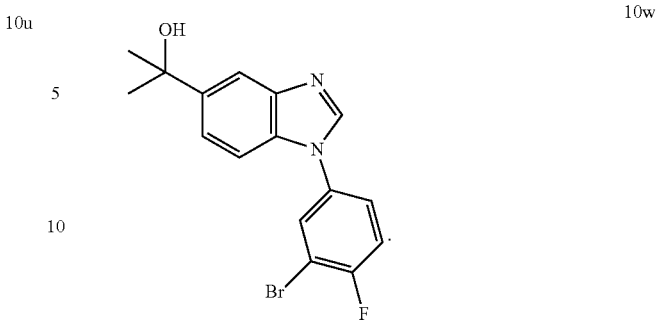
10w

Novel intermediates 10k-10q and 10s-10u may be prepared as described below in Schemes 5-10.

In another set of embodiments, any atom not designated as deuterium in any of the embodiments set forth above is present at its natural isotopic abundance.

The synthesis of compounds of Formula I, Ia and II may be readily achieved by synthetic chemists of ordinary skill by reference to the Exemplary Synthesis and Examples disclosed herein. Relevant procedures analogous to those of use for the preparation of compounds of Formula I, Formula Ia and intermediates thereof are disclosed, for instance in WO 07/110,374.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

Compounds of Formula I, Ia and II may be prepared according to the schemes shown below.

Scheme 1: General Route to Compounds of Formula I.

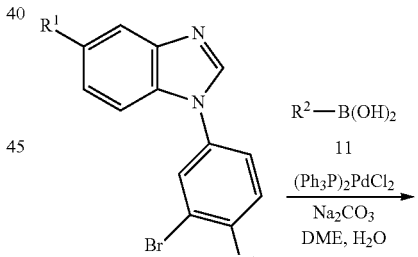

10, wherein $R^6$ is $R^1$
and X is ——Br

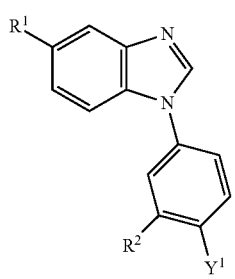

Formula I

Scheme 1 depicts a general route to preparing compounds of Formula I. Palladium-catalyzed coupling of appropriately-substituted aryl bromide 10, wherein $R^6$ is $R^1$, with the appropriate boronic acid 11 affords compounds of Formula I. Useful boronic acids 11 include commercially available materials such as 2-cyanophenylboronic acid, (2-cyano-6-fluorophenyl)boronic acid, 2-fluoropyridine-3-boronic acid, pyridine-3-boronic acid, 4-fluoro-pyridine-3-boronic acid, 4-methylpyridine-3-boronic acid, 2-chlorophenylboronic acid, 5-chloro-2-methoxyphenylboronic acid, and 5-fluoro-2-methoxyphenylboronic acid. Additional useful boronic acids 11 also include 5-fluoro-2-(methoxy-$d_3$)phenylboronic acid and 5-chloro-2-(methoxy-$d_3$)phenylboronic acid. Preparation of these compounds is described in Schemes 11a and 11b.

Scheme 2: Alternate Route to Compounds of Formula I, wherein $R^1$ is —$CR^3$=$NOR^4$ and $R^3$ is H or D.

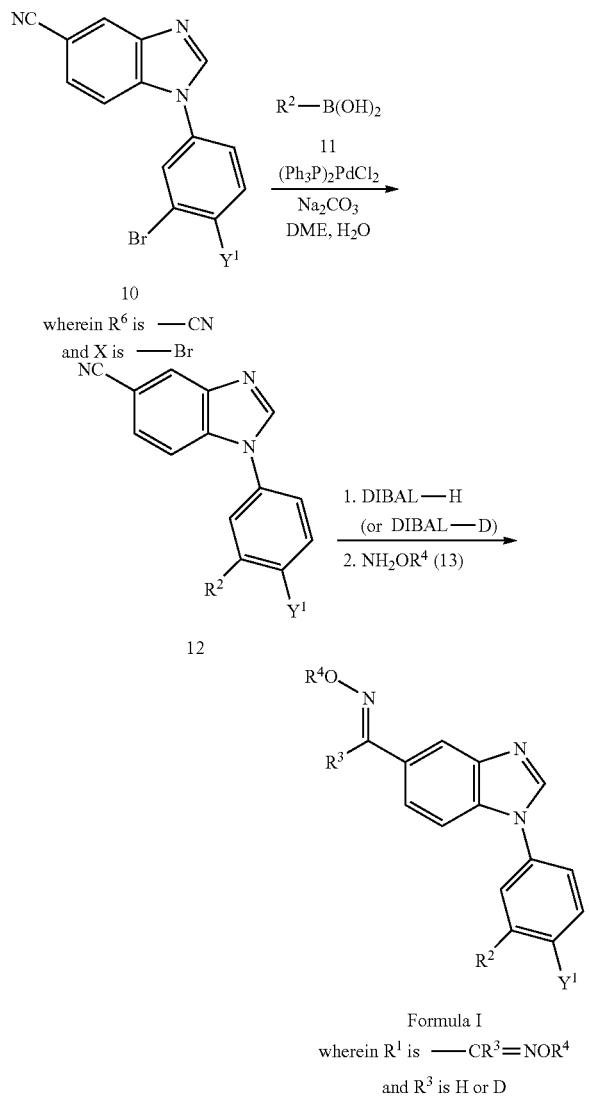

Scheme 2 depicts an alternate route to compounds of Formula I, wherein $R^1$ is —$CR^3$=$NOR^4$ and $R^3$ is H or D, which is analogous to that disclosed in WO 07/110,374. Appropriately-substituted intermediate 10, wherein $R^6$ is —CN, undergoes palladium-catalyzed coupling with an appropriately-substituted boronic acid 11 to afford compound 12. Compound 12 may be converted to compounds of Formula I via DIBAL-H or DIBAL-D reduction of the nitrile moiety, followed by condensation with an appropriately-substituted amine 13.

Scheme 3: Additional Route to Compounds of Formula I.

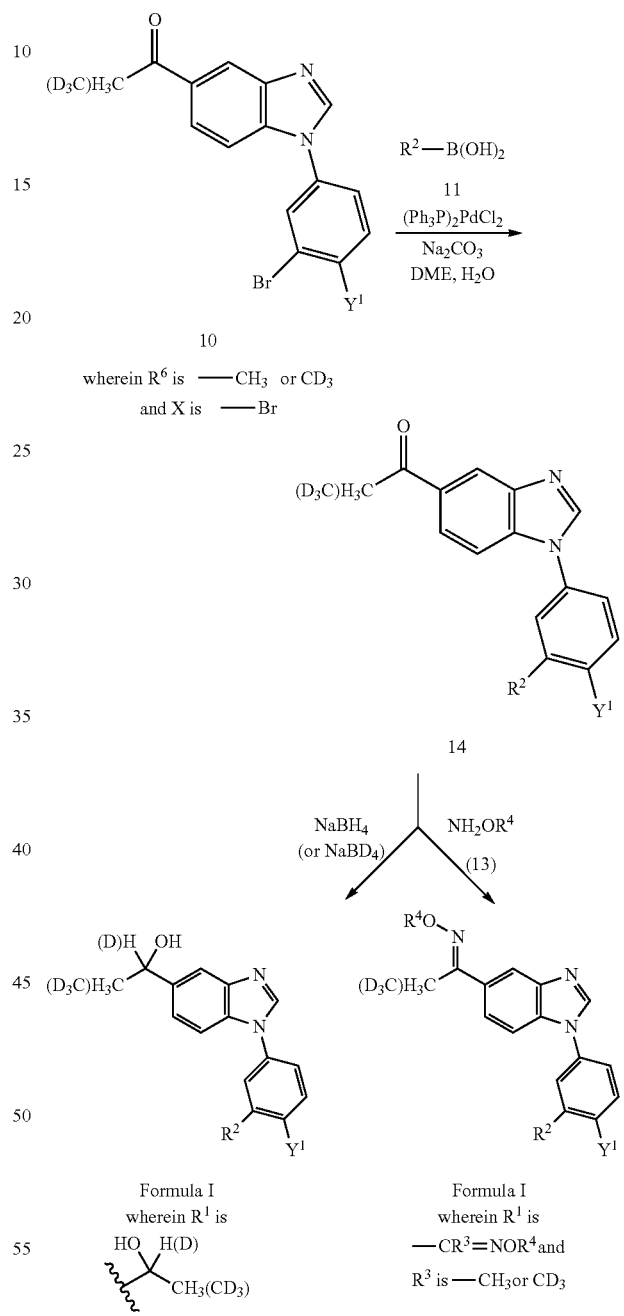

Scheme 3 depicts an additional route to compounds of Formula I, in a manner analogous to that disclosed in WO 07/110,374. Appropriately-substituted intermediate 10, wherein $R^6$ is —$CH_3$ or —$CD_3$, undergoes palladium-catalyzed coupling with an appropriately-substituted boronic acid 11 to afford compound 14. Compound 14 may be converted to compounds of Formula I via either $NaBH_4$ (or $NaBD_4$) reduction of the carbonyl moiety, or by condensation with an appropriately-substituted amine 13.

Scheme 4: Alternate Route to Compounds of Formula Ia, wherein Z is —C(OH)(CH₃)₂, —C(OH)(CD₃)₂, or —C(OH)(CH₃)CD₃.

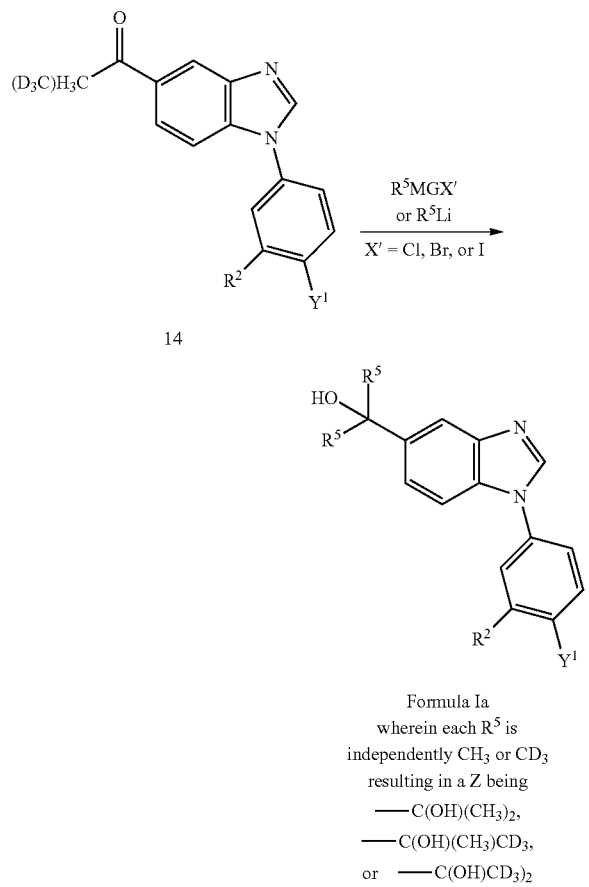

14

Formula Ia
wherein each R⁵ is independently CH₃ or CD₃ resulting in a Z being
—C(OH)(CH₃)₂,
—C(OH)(CH₃)CD₃,
or —C(OH)(CD₃)₂

Scheme 4 depicts an alternate route to compounds of Formula Ia, wherein Z is —C(OH)(CH₃)₂ (each R⁵ is —CH₃), —C(OH)(CH₃)CD₃ (R⁵ is both —CH₃ and —CD₃) or —C(OH)(CD₃)₂ (each R⁵ is —CD₃). Compound 14 may be treated with an appropriately-substituted Grignard reagent or alkyl lithium reagent to afford compounds of Formula Ia, wherein Z is —C(OH)(CH₃)₂ or —C(OH)(CD₃)₂.

Scheme 5: Preparation of Intermediate 10k.

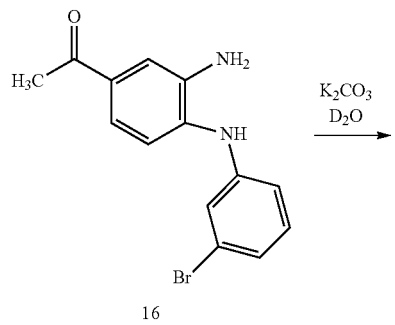

16

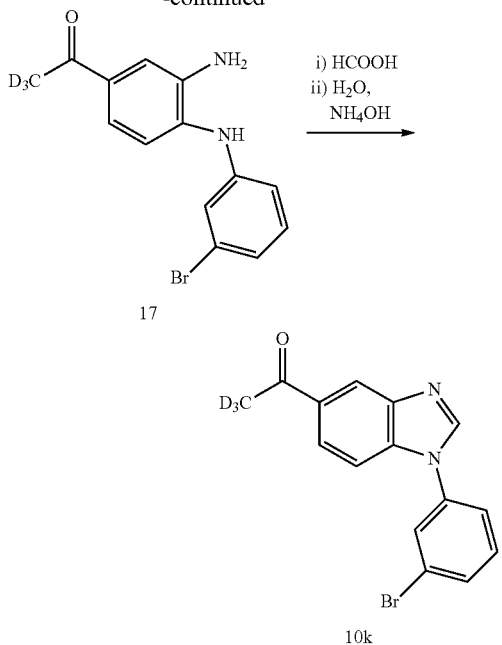

17

10k

Scheme 5 depicts the synthesis of novel deuterated intermediate 10k in a manner analogous to the methods disclosed in WO 07/110,374. Thus, ketone 16 is treated with potassium carbonate and D₂O to effect a hydrogen-to-deuterium exchange. The resulting deuterated ketone 17 is treated with formic acid, followed by aqueous NH₄OH, to afford intermediate 10k. To maximize the levels of deuterium incorporation, deuterated reagents and solvents may be useful in the conversion of 17 to 10k.

Scheme 5b: Preparation of Intermediate 10t.

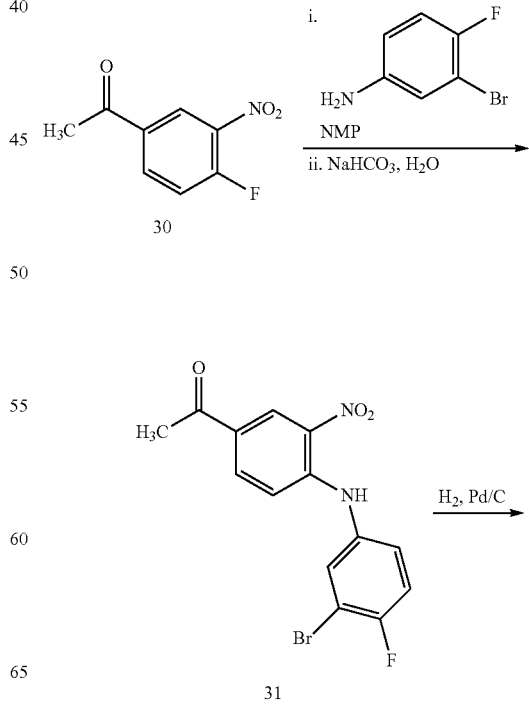

30

31

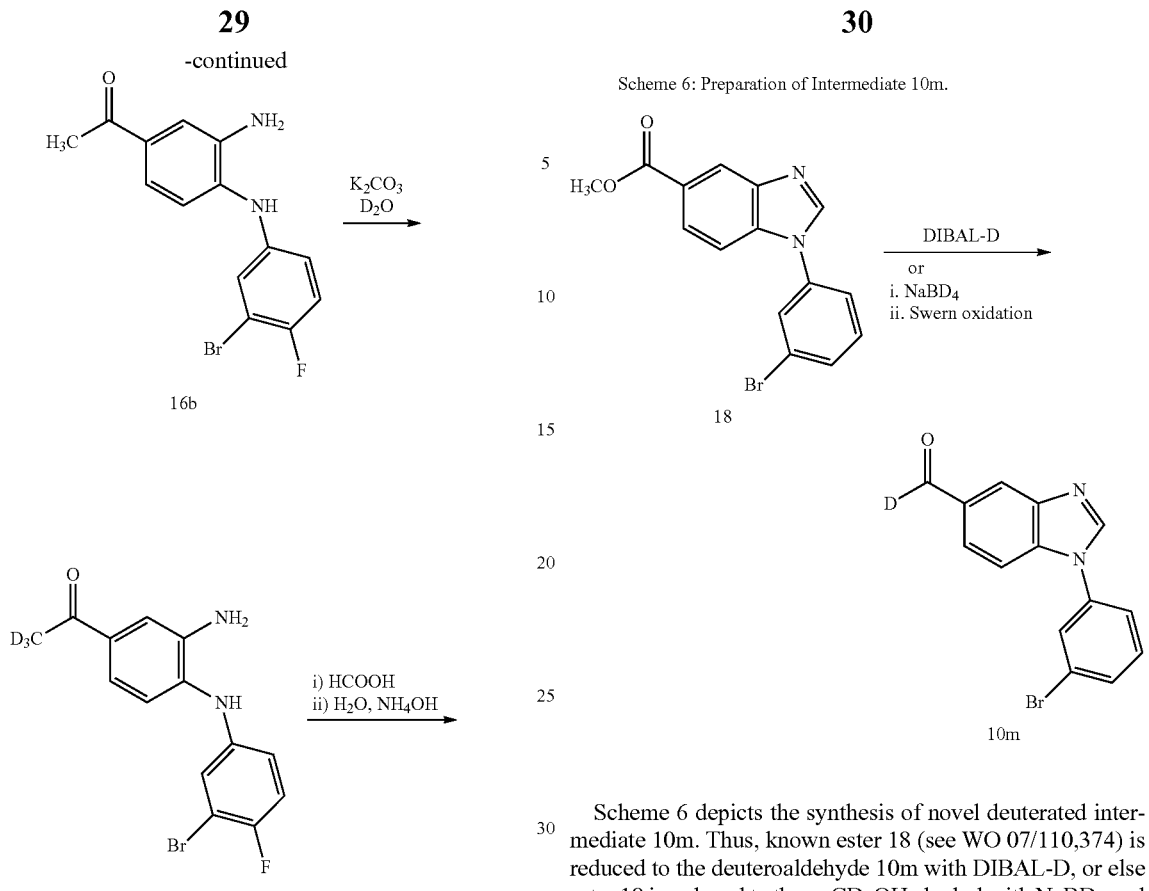

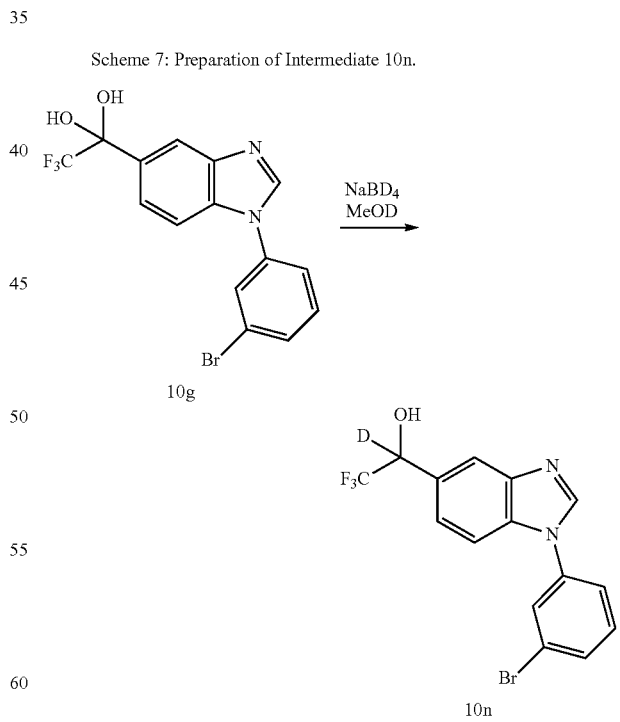

Scheme 6 depicts the synthesis of novel deuterated intermediate 10m. Thus, known ester 18 (see WO 07/110,374) is reduced to the deuteroaldehyde 10m with DIBAL-D, or else ester 18 is reduced to the —CD₂OH alcohol with NaBD₄ and then oxidized to afford 10m.

Scheme 5b depicts the synthesis of novel deuterated intermediate 10t in a manner analogous to the methods disclosed in WO 96/033191. Thus, known ketone 30 is treated with commercially available 3-bromo-4-fluoroaniline in NMP, followed by treatment with aqueous sodium bicarbonate to afford ketone 31. Reduction of the nitro group of 31 with hydrogen gas and palladium on carbon (or alternatively with H₂/Raney Nickel, SnCl₂/HCl, Fe/HCl, or Fe/NH₄Cl) provides ketone 16b. Ketone 16b is treated with potassium carbonate and D₂O to effect a hydrogen-to-deuterium exchange. The resulting deuterated ketone 17b is treated with formic acid, followed by aqueous NH₄OH, to afford intermediate 10t. To maximize the levels of deuterium incorporation, deuterated reagents and solvents may be useful in the conversion of 17b to 10t.

Scheme 7 depicts the synthesis of novel deuterated intermediate 10n in a manner analogous to the methods disclosed in WO 07/110,374. Thus, known intermediate 10g is reduced with NaBD₄ to afford 10n.

Scheme 8: Preparation of Intermediate 10p.

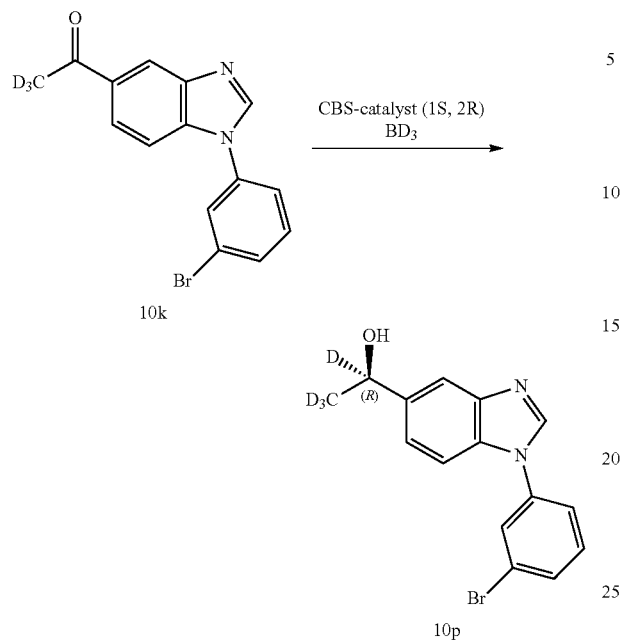

Scheme 8 depicts the synthesis of novel deuterated intermediate 10p in a manner analogous to the methods disclosed in WO 07/110,374. Thus, intermediate 10k is reduced with CBS-catalyst (1S,2R)-cis-1-amino-2-indanol and $BD_3$ to afford 10p.

Scheme 9: Preparation of Intermediates 10q and 10u.

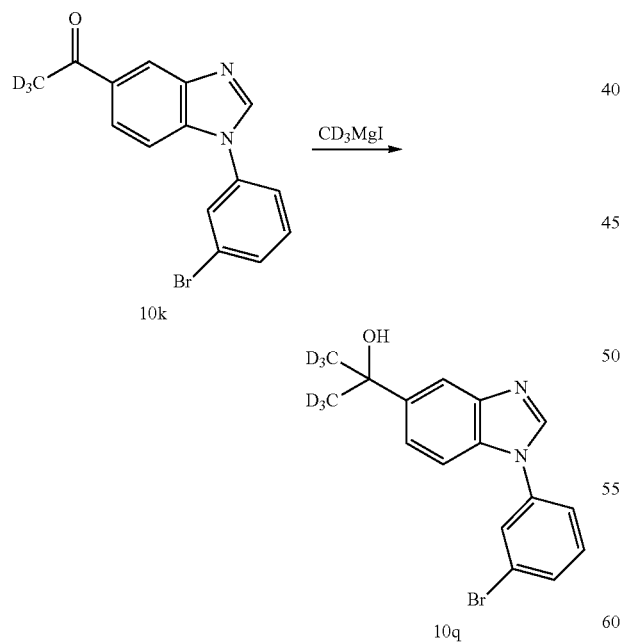

Scheme 9 depicts the synthesis of novel deuterated intermediate 10q in a manner analogous to the methods disclosed in WO 07/110,374. Thus, intermediate 10k is treated with $CD_3MgI$ to afford 10q. In the same manner, intermediate 10t is converted to 10u via treatment with $CD_3MgI$.

Scheme 10: Preparation of Intermediate 10s.

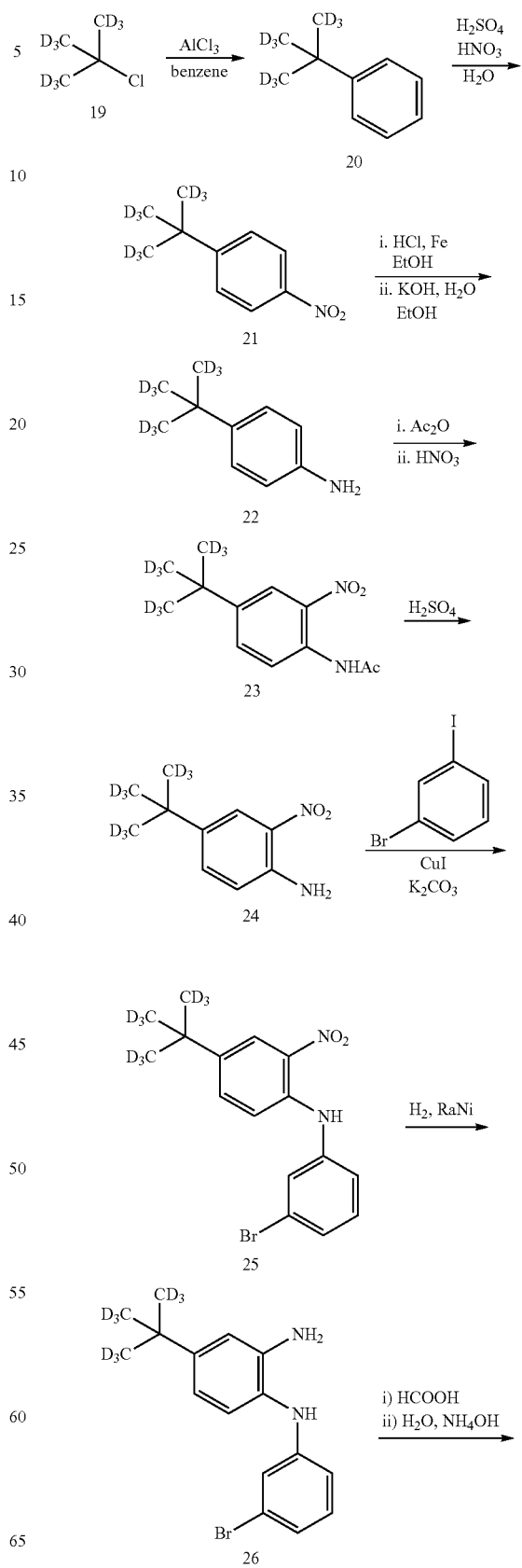

-continued

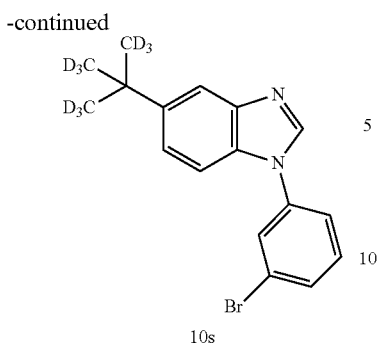

10s

Scheme 10 depicts the synthesis of novel deuterated intermediate 10s. Thus, t-butyl chloride-d9 and benzene are converted to 20 by treatment with AlCl₃ (in a manner analogous to that disclosed in Cai, Z. et al., Nongyao, 2002, 41(12):16-17) or by treatment with ZnCl₂ on silica (in a manner analogous to that disclosed in Japanese patent application JP 2002095971). In a manner analogous to the methods disclosed in Langhals, H., New Journal of Chemistry, 2008, 32(1):21-23, 20 is treated with sulfuric acid and nitric acid to provide aryl nitro compound 21, which is then reduced to aniline 22 via treatment with iron and HCl. In a manner analogous to that disclosed in EP 616807, aniline 22 is then converted to nitroaniline 25 by sequential treatment with acetic anhydride, then with nitric acid, then with sulfuric acid, then with copper iodide and 1-bromo-3-iodobenzene. In a manner analogous to that disclosed in WO 07/110,374, 25 is reduced with hydrogen in the presence of Raney Nickel to afford diamine 26, which is treated with formic acid followed by aqueous NH₄OH to afford 10s. Alternate conditions for the reduction of the nitro group include H₂/Pd—C, SnCl₂/HCl, Fe/HCl, or Fe/NH₄Cl.

Scheme 11a: Preparation of 5-Chloro-2-(methoxy-d₃)phenylboronic acid (11a).

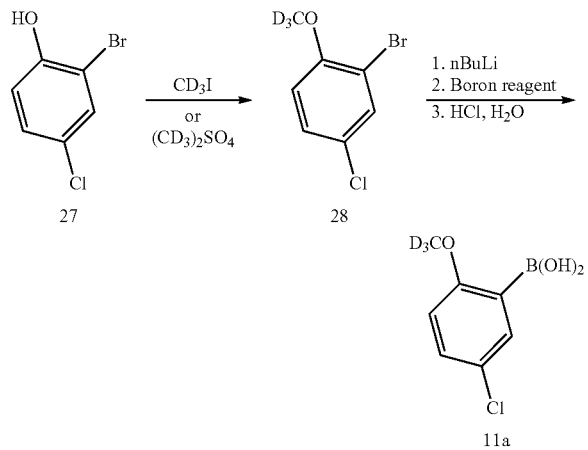

Scheme 11a depicts the preparation of an example of boronic acid 11, 5-chloro-2-(methoxy-d₃)phenylboronic acid (11a). Thus, commercially available 2-bromo-4-chlorophenol 27 is treated with either CD₃I (in a manner analogous to that described in Dyke, A. M. et al., Angew. Chem. Intl. Ed., 2008, 47(27):5067-5070) or with (CD₃)₂SO₄ (in a manner analogous to that described in Deng, B.-L. et al., J. Med. Chem., 2005, 48(19):6140-6155) to afford ether 28. Treatment with nBuLi, followed by an appropriate boron reagent and then by acidic hydrolysis, provides 11a. For the boron reagent, B(OiPr)₃ may be used in a manner analogous to that of Davies, C. J. et al., Tetrahedron, 2008, 64(42):9857-9864, or KB(iPr)₃H or K-Selectride may be used in a manner analogous to that described in WO 2005019151.

Scheme 11b: Preparation of 5-Fluoro-2-(methoxy-d₃)phenylboronic acid (11b).

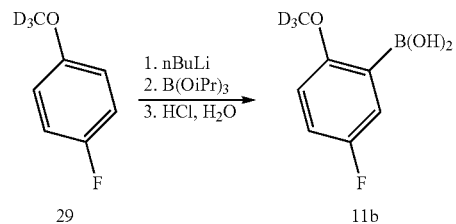

Scheme 11b depicts the preparation of an example of boronic acid 11, 5-fluoro-2-(methoxy-d₃)phenylboronic acid (11b). Thus, known compound 29 (see Forsyth, D. A.; et al., J.A.C.S., 1986, 108(9):2157-2161) is treated with nBuLi, followed by B(OiPr)₃ and then by acidic hydrolysis to provide 11b in a manner analogous to that described in Audouze, K. et al., J. Med. Chem., 2004, 47(12):3089-3104.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art. Combinations of substituents and variables envisioned by this invention are only those that result in the formation of stable compounds.

Compositions

The invention also provides pyrogen-free compositions comprising a compound of Formula I (e.g., including any of the formulae herein), or a pharmaceutically acceptable salt of said compound; and an acceptable carrier. In one embodiment, the composition comprises an effective amount of the compound of Formula I. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz, J D and Zaffaroni, A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound that modulates the $GABA_A$ receptor.

Preferably, the second therapeutic agent is an agent useful in the treatment or prevention of a disease or condition selected from anxiety disorders such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; convulsions; depressive or bipolar disorders, for example singe-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; speech disorders, including stuttering; and disorders of circadian rhythm, for example in subjects suffering from the effects of jet lag or shift work; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, for example in paraplegic patients; hearing disorders, including tinnitus and age-related hearing impairment; urinary incontinence; and the effects of substance abuse and dependency, including alcohol withdrawal; athetosis, epilepsy, stiff-person syndrome, pain and nociception; and other disorders of the central nervous system.

In a particular embodiment, the disease or condition is selected from anxiety, convulsions, skeletal muscle spasm, spasticity, athetosis, epilepsy, stiff-person syndrome, other disorders of the central nervous system, and pain (e.g., neuropathic pain, inflammatory pain, and migraine-associated pain). In a particular embodiment, the disease is selected from anxiety and convulsions.

Examples of pain include acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, and cancer pain. More particular examples include femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, including abdominal, pancreatic, and IBS pain; chronic and acute headache pain; migraine; tension headache, including cluster headaches; chronic and acute neuropathic pain, including post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, including abdominal pain, pyelonephritis, appendicitis, cholecystitis, intestinal obstruction, and hernias; chest pain, including cardiac pain; pelvic pain; renal colic pain; acute obstetric pain, including labor pain; cesarean section pain; acute inflammatory, burn and trauma pain; acute intermittent pain, including endometriosis; acute herpes zoster pain; sickle cell anemia; acute pancreatitis; breakthrough pain; orofacial pain including sinusitis pain and dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; painful bladder syndrome; interstitial cystitis (IC); prostatitis; complex regional pain syndrome (CRPS), type I and type II; and angina-induced pain. For example, the pain may be pain selected from the group consisting of fibromyalgia, acute herpes zoster pain, HIV-associated neuropathy, neuropathic low back pain, chemotherapy induced neuropathic pain, radiotherapy-induced neuropathic pain, peripheral nerve injury, spinal cord injury pain, and multiple sclerosis (MS) pain.

In one embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In one embodiment of the pharmaceutical compositions of the invention, the compound of the present invention is present in an effective amount. As used herein, the term "effective amount" refers to an amount which, when administered in a proper dosing regimen, is sufficient to treat a disease or disorder, or enhance or improve the prophylactic or therapeutic effect(s) of another therapy.

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In one embodiment, an effective amount of a compound of this invention can range from about 0.01 to about 5000 mg per treatment. In more specific embodiments the range is from about 0.1 to 2500 mg, or from 0.2 to 1000 mg, or most specifically from about 1 to 500 mg. Treatment typically is administered one to three times daily.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

According to another embodiment, the invention provides a method of treating a disease or condition that is beneficially treated by a compound that modulates the $GABA_A$ receptor in a subject, comprising the step of administering to said subject an effective amount of a compound of this invention or a pharmaceutically acceptable salt of said compound or a composition of this invention. Such diseases are well known in the art and are disclosed in, but not limited to the following patents and published applications: WO 1998004559, WO 2000044752, WO 2006061428 and U.S. Pat. No. 6,630,471. Such diseases or conditions include, but are not limited to, anxiety disorders such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; convulsions; depressive or bipolar disorders, for example singe-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; speech disorders, including stuttering; and disorders of circadian rhythm, for example in subjects suffering from the effects of jet lag or shift work; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, for example in paraplegic patients; hearing disorders, including tinnitus and age-related hearing impairment; urinary incontinence; and the effects of substance abuse and dependency, including alcohol withdrawal; athetosis, epilepsy, stiff-person syndrome, pain and nociception; and other disorders of the central nervous system.

In a particular embodiment, the disease or condition is selected from anxiety, convulsions, skeletal muscle spasm, spasticity, athetosis, epilepsy, stiff-person syndrome, other disorders of the central nervous system, and pain (e.g., neuropathic pain, inflammatory pain, and migraine-associated pain). In a particular embodiment, the disease is selected from anxiety and convulsions.

In one embodiment, the disease is pain selected from the group consisting of: acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head pain, neck pain, severe or intractable pain, nociceptive pain, breakthrough pain, postsurgical pain, and cancer pain.

In another embodiment, the pain is selected from the group consisting of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, including abdominal, pancreatic, and IBS pain; chronic and acute headache pain; migraine; tension headache, including cluster headaches; chronic and acute neuropathic pain, including post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, including abdominal pain, pyelonephritis, appendicitis, cholecystitis, intestinal obstruction, and hernias; chest pain, including cardiac pain; pelvic pain; renal colic pain; acute obstetric pain, including labor pain; cesarean section pain; acute inflammatory, burn and trauma pain; acute intermittent pain, including endometriosis; acute herpes zoster pain; sickle cell anemia; acute pancreatitis; breakthrough pain; orofacial pain including sinusitis pain and dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; painful bladder syndrome; interstitial cystitis (IC); prostatitis; complex regional pain syndrome (CRPS), type I and type II; and angina-induced pain.

In yet another embodiment, the pain is selected from the group consisting of: fibromyalgia, acute herpes zoster pain, HIV-associated neuropathy, neuropathic low back pain, chemotherapy induced neuropathic pain, radiotherapy-induced neuropathic pain, peripheral nerve injury, spinal cord injury pain, and multiple sclerosis (MS) pain.

Methods delineated herein also include those wherein the subject is identified as in need of a particular stated treatment. Identifying a subject in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to said subject one or more second therapeutic agents. The choice of second therapeutic agent may be made from any second therapeutic agent known to be useful for co-administration with a compound that modulates the $GABA_A$ receptor. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

The term subject can include a patient in need of treatment.

In yet another aspect, the invention provides the use of a compound of Formula I, or a pharmaceutically acceptable salt of said compound, alone or together with one or more of the above-described second therapeutic agents in the manufacture of a medicament, either as a single composition or as separate dosage forms, for treatment or prevention in a subject of a disease, disorder or symptom set forth above. Another aspect of the invention is a compound of Formula I for use in the treatment or prevention in a subject of a disease, disorder or symptom thereof delineated herein.

EXAMPLES

Example 1

3'-(5-(2-Hydroxy-1,1,1,3,3,3-$d_6$-propan-2-yl)-1H-benzo[d]imidazol-1-yl)biphenyl-2-carbonitrile (Compound 102)

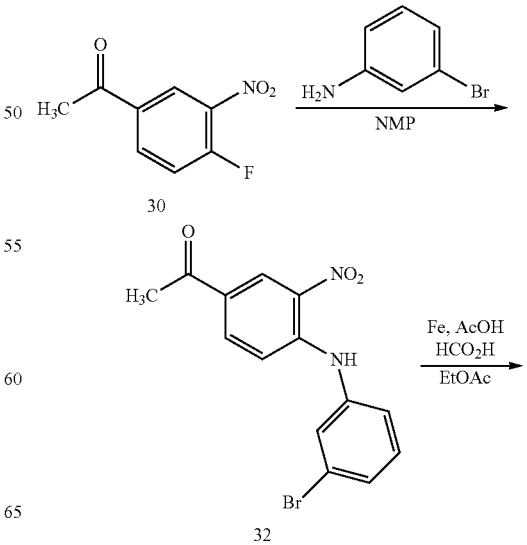

Scheme 12. Preparation of Compound 102.

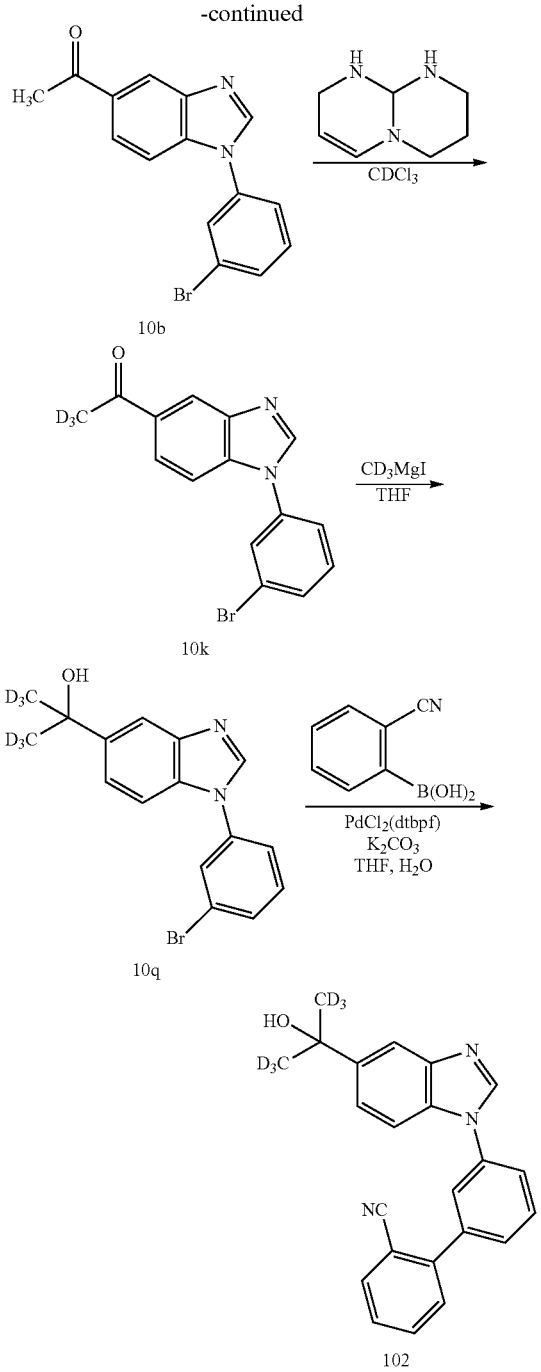

Step 1. 1-(4-(3-Bromophenylamino)-3-nitrophenyl)ethanone (32): A solution of 4-fluoro-3-nitro-acetophenone 30 (5.0 g, 27.3 mmol) and 3-bromoaniline (5.64 g, 43.6 mmol) in NMP (20 mL) was heated at 80° C. (bath temperature) under a nitrogen atmosphere for three days. The cooled mixture was poured into water (100 mL). The red precipitate was filtered and washed with water (2×20 mL), then heptanes (3×20 mL). The solid was dried under vacuum (45° C.) for 6 hours to afford 9.2 g (95%) of 32 with 95% purity.

Step 2. 1-(1-(3-Bromophenyl)-1H-benzo[d]imidazol-5-yl)ethanone (10b): A mixture of crude 32 (8.2 g, 24.4 mmol), formic acid (100 mL), acetic acid (100 mL) and EtOAc (100 mL) was heated to 60-70° C. Iron (21 g, 366 mmol) was then added. After 3 hours additional iron (10 g, followed later by 5 g) was added and heating was continued for 30 hours until the reaction was complete. The cooled mixture was filtered through a pad of silica gel topped with Celite, washing with EtOAc (100 mL). The filtrate was concentrated to dryness. $CH_2Cl_2$ (100 mL) was added to dissolve all the solids then the solution was concentrated to approximately 30 mL volume. The precipitate was collected and the filtrate was further concentrated to yield a second crop of product. The solids were combined to give 4.8 g of 10b as light yellow solid. The mother liquor was purified on silica gel eluting with 50-100% EtOAc/heptanes to give another 2 g of 10b (total yield 88%).

Step 3. 1-(1-(3-Bromophenyl)-1H-benzo[d]imidazol-5-yl)-2,2,2,-$d_3$-ethanone (10k): 10b (4.8 g, 15.2 mmol was dissolved in $CDCl_3$ (Cambridge Isotopes, 99.9 atom % D; 50 mL) then 2,3,4,6,7,8-hexahydro-1H-pyrimido[1,2-a]pyrimidine (105 mg, 0.75 mmol) was added. The cloudy solution was stirred at room temperature overnight. $^1$H NMR showed ~8% proton remained on the α-carbon. The solution was concentrated to dryness and passed through a silica gel column eluting with 50-100% EtOAc/heptanes to give 3.1 g of the first cycle product. This exchange process was repeated twice to achieve less than 2% proton remaining on the α-carbon. The mixture was concentrated to dryness and used directly in the next step.

Step 4. 2-(1-(3-Bromophenyl)-1H-benzo[d]imidazol-5-yl)propan-$d_6$-2-ol (10q): Crude 10k (1.5 g, 4.7 mmol) was suspended in anhydrous THF (30 mL) and cooled in an ice water bath. $CD_3MgI$ (Aldrich, 99+ atom % D; 1M in ether, 9 mL) was added and the mixture stirred for 30 minutes. The cold bath was removed and the mixture was stirred at room temperature for 2 hours. The reaction was quenched with saturated aqueous ammonium chloride solution (30 mL) and the mixture was extracted with EtOAc (3×80 mL). The combined organic phases were dried ($Na_2SO_4$), and concentrated. The crude material was purified on an Analogix automated chromatography system eluting with 0-70% EtOAc/heptanes to give 1.25 g (76%) of 10q. Alternatively, the crude product was purified on an Analogix automated chromatography system eluting with 30-100% EtOAc/heptanes to give a yellow syrup that slowly solidified on standing. The material was further purified by trituration with EtOAc/heptanes (1:3, 20 mL) to provide 10q. MS (M+H): 339.0.

Step 5. 3'-(5-(2-Hydroxy-1,1,1,3,3,3-$d_6$-propan-2-yl)-1H-benzo[d]imidazol-1-yl)biphenyl-2-carbonitrile (Compound 102): 10q (1.2 g, 3.56 mmol) was mixed with 2-cyano-benzeneboronic acid (740 mg, 5 mol) and $K_2CO_3$ (1.22 g, 8.9 mmol) in THF (20 mL) and water (10 mL). Nitrogen was bubbled through the mixture for 5 minutes. Bis(di-t-butylphosphine)ferrocenepalladium(II)dichloride (0.1 g, 0.15 mmol) was added and the mixture was heated at 75° C. (bath temperature) overnight. The mixture was extracted with EtOAc (3×50 mL), the combined organic phases dried ($Na_2SO_4$), and concentrated. The crude material was purified on an Analogix system eluting with 0-3% MeOH/$CH_2Cl_2$ to give a mixture of the starting material and the desired product. This mixture was re-subjected to the reaction conditions to drive the reaction to completion. The crude product was then purified on an Analogix system eluting with 0-3% MeOH/DCM to give 525 mg (41%) of 102. This material was further purified on an Analogix reverse-phase C18 column eluting with 0-70% MeOH/water to give pure 102. $^1$H-NMR (300 MHz, $CDCl_3$): δ 2.45 (br s, 1H), 7.49-7.78 (m, 9H), 8.02 (s, 1H), 8.29 (s, 1H). $^{13}$C-NMR (75 MHz, $CDCl_3$): δ 109.94, 111.41, 116.89, 118.50, 122.05, 123.77, 124.07, 128.06, 128.33, 130.05, 130.57, 131.41, 133.10, 133.90, 137.00, 140.16, 142.18, 143.97, 144.24, 146.48. HPLC (method: Waters Atlantis T3 2.1 column 2.1×50 mm 3 μm—gradient method 5-95% ACN+0.1% formic acid in 14 min with 4 min hold at 95% ACN+0.1% formic acid; wavelength: 190 nm): retention time: 6.26 min; 99.2% purity. MS (M+H): 360.3. Elemental Analysis ($C_{23}H_{13}D_6N_3O$): Calculated: C=76.86; H=5.33; N=11.69. Found: C=72.54; H=4.53; F=4.85; N=10.60.

Example 2

3'-(5-tert-Butyl-$d_9$-1H-benzo[d]imidazol-1-yl)biphenyl-2-carbonitrile (Compound 103)

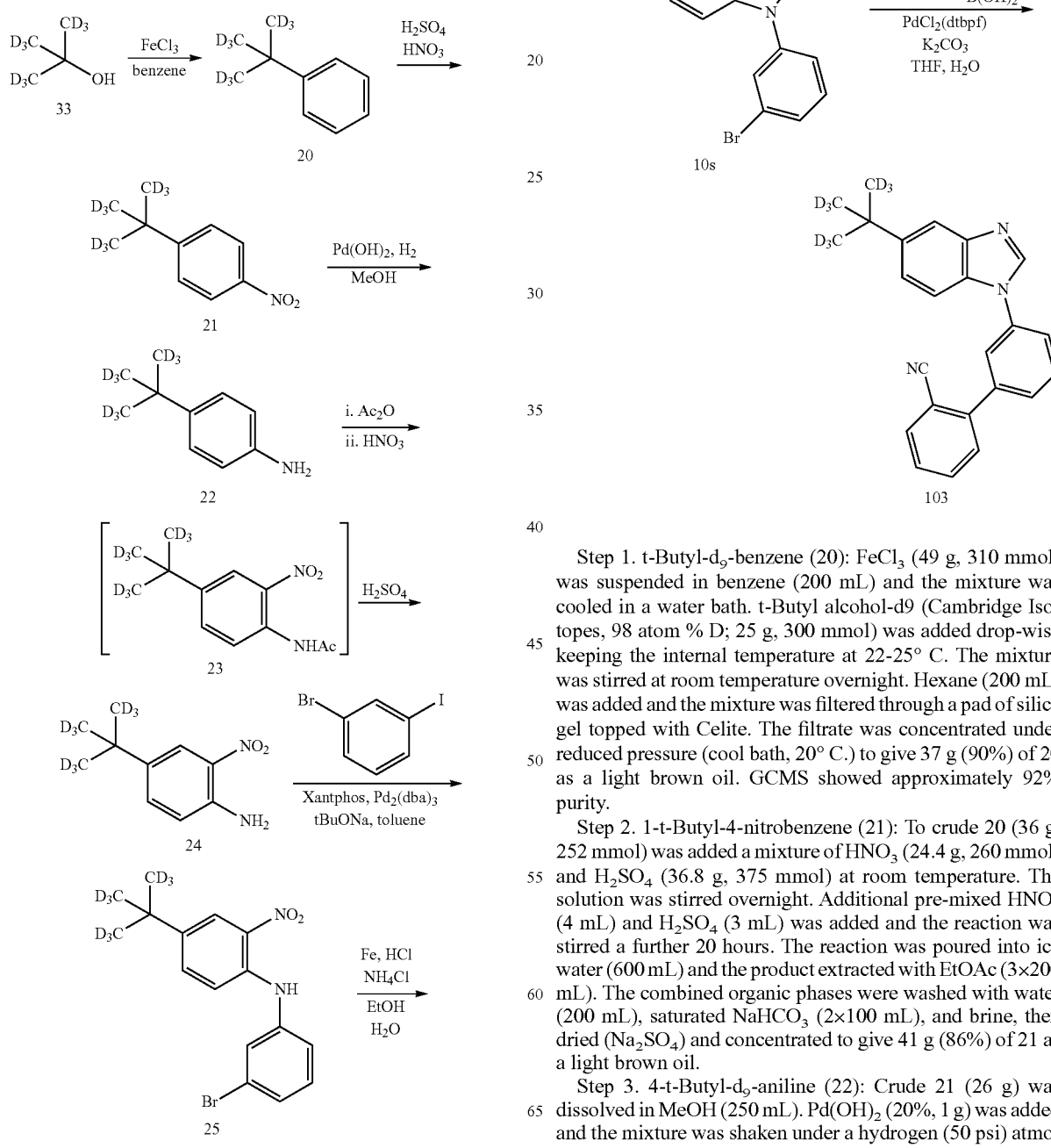

Step 1. t-Butyl-$d_9$-benzene (20): FeCl$_3$ (49 g, 310 mmol) was suspended in benzene (200 mL) and the mixture was cooled in a water bath. t-Butyl alcohol-d9 (Cambridge Isotopes, 98 atom % D; 25 g, 300 mmol) was added drop-wise keeping the internal temperature at 22-25° C. The mixture was stirred at room temperature overnight. Hexane (200 mL) was added and the mixture was filtered through a pad of silica gel topped with Celite. The filtrate was concentrated under reduced pressure (cool bath, 20° C.) to give 37 g (90%) of 20 as a light brown oil. GCMS showed approximately 92% purity.

Step 2. 1-t-Butyl-4-nitrobenzene (21): To crude 20 (36 g, 252 mmol) was added a mixture of HNO$_3$ (24.4 g, 260 mmol) and H$_2$SO$_4$ (36.8 g, 375 mmol) at room temperature. The solution was stirred overnight. Additional pre-mixed HNO$_3$ (4 mL) and H$_2$SO$_4$ (3 mL) was added and the reaction was stirred a further 20 hours. The reaction was poured into ice water (600 mL) and the product extracted with EtOAc (3×200 mL). The combined organic phases were washed with water (200 mL), saturated NaHCO$_3$ (2×100 mL), and brine, then dried (Na$_2$SO$_4$) and concentrated to give 41 g (86%) of 21 as a light brown oil.

Step 3. 4-t-Butyl-$d_9$-aniline (22): Crude 21 (26 g) was dissolved in MeOH (250 mL). Pd(OH)$_2$ (20%, 1 g) was added and the mixture was shaken under a hydrogen (50 psi) atmosphere for 3 hours until no further hydrogen uptake was observed. The mixture was filtered through a pad of Celite. The filtrate was concentrated to give approximately 20 g of 22. This material was used directly in the next step.

Step 4. 4-t-Butyl-d₉-2-nitroaniline (24): Crude 22 (15 g, 95 mmol) was dissolved in acetic anhydride (120 mL). Nitric acid (70%, 10 mL) was added and the mixture was stirred overnight at room temperature. The solution was poured into ice water (500 mL) and the yellow solid was filtered and dried to give crude 23. The crude 23 was added to a mixture of water (25 mL) and sulfuric acid (50 mL) and the mixture was heated at 100° C. for 2 hours, then stirred at room temperature for a further 6 hours. The solution was poured into ice water and the solid was filtered. The solid was dissolved in EtOAc (300 mL) and the solution was washed with water (100 mL), saturated NaHCO₃ (100 mL), brine, then dried (Na₂SO₄) and concentrated. The crude product was purified on a silica gel column eluting with 1:9 EtOAc/heptanes to give 11 g (54% over two steps) of 24.

Step 5. N-(3-Bromophenyl)-4-t-butyl-d₉-2-nitroaniline (25): To a sealed tube was added 24 (1.95 g, 9.6 mmol), 3-bromoiodobenzene (3 g, 10.6 mmol), Xantphos (174 mg, 0.3 mmol), sodium tert-butoxide (1.44 g, 15 mmol) and toluene (20 mL). The mixture was purged with nitrogen for 5 minutes then tris(dibenzylideneacetone)dipalladium(0) (Pd₂(dba)₃, 92 mg, 0.1 mmol) was added. The tube was sealed and heated at 100° C. for 5 hours. The cooled reaction mixture was filtered through a pad of Celite, washing with EtOAc (100 mL). The filtrate was adsorbed onto silica gel and dry loaded on a silica gel column eluting with 0-1:6 EtOAc/heptanes to give 2.4 g (70%) of 25 as a red solid.

Step 6. 1-(3-Bromophenyl)-5-t-butyl-d₉-1H-benzo[d]imidazole (10s): To iron powder (1.87 g, 33.5 mmol) in EtOH (20 mL) was added HCl (12 N, 0.28 mL) and the mixture was stirred for 1 hour at 50° C. Aqueous ammonium chloride solution (25% w/v, 10 mL) was added followed by a solution of 25 (2.4 g, 6.7 mmol) in EtOH (total 8 mL). The mixture was heated at 60-70° C. for 3 hours then was filtered through a pad of Celite, washing with EtOAc (100 mL). The filtrate was concentrated to dryness. Formic acid (18 mL) was added and the mixture was heated at 80° C. for 2 hours. The reaction was cooled and concentrated. The residue was dissolved in EtOAc (100 mL) and the organic solution was washed with water, saturated NaHCO₃, and brine, then dried (Na₂SO₄), and concentrated. The product was purified on a silica gel column eluting with 1:1 EtOAc/heptanes to give 1.9 g (84%) of 10s. Alternatively the material was purified on an Analogix automated chromatography system eluting with 0-70% EtOAc/heptanes, followed by trituration with EtOAc/heptanes (1:2, 20 mL) to provide 10s. 1H-NMR (300 MHz, CDCl₃): δ 7.40-7.51 (m, 4H), 7.59 (td, J=2.0, 7.1), 7.68-7.71 (m, 1H), 7.88 (dd, J=0.7, 1.8, 1H), 8.07 (s, 1H).

Step 7. 3'-(5-t-Butyl-d₉-1H-benzo[d]imidazol-1-yl)biphenyl-2-carbonitrile (Compound 103): A mixture of 10s (1.5 g, 4.4 mmol), 2-cyanobenzeneboronic acid (1.14 g, 7.8 mmol) and K₂CO₃ (2.07 g, 15 mmol) in THF (20 mL) and water (10 mL) was purged with nitrogen for 5 minutes. Bis(di-t-butylphosphine)ferrocenepalladium(II) dichloride (0.15 g, 0.23 mmol) was added and the mixture was heated at 50° C. for 24 hours. The reaction mixture was diluted with water (20 mL) and extracted with EtOAc (3×50 mL). The combined organic phases were dried (Na₂SO₄) and concentrated. The crude product was purified on an Analogix automated chromatography system eluting with 0-2% MeOH/CH₂Cl₂. Concentration of product fractions gave a sticky semi-solid. This material was further purified on an Analogix reverse-phase C18 column eluting with 0-100% MeOH/water to give 720 mg (46%) of 103. ¹H-NMR (300 MHz, CDCl₃): δ 7.45 (dd, J=1.8, 8.8, 1H), 7.52 (dt, J=1.2, 7.8, 1H), 7.55-7.57 (m, 0.4H), 7.58-7.66 (m, 3.1H), 7.67-7.75 (m, 3.4H), 7.83 (app ddd, J=0.5, 1.2, 7.61, 1H), 7.90 (app dd, J=0.4, 1.8, 1H), 8.16 (s, 1H). ¹³C-NMR (75 MHz, CDCl₃): δ 110.46, 111.39, 115.92, 121.51, 123.96, 124.26, 128.42, 128.52, 130.05, 130.69, 133.15, 133.91, 140.28. HPLC (method: Waters Atlantis T3 2.1 column 2.1×50 mm 3 μm—gradient method 5-95% ACN+0.1% formic acid in 14 min with 4 min hold at 95% ACN+0.1% formic acid; wavelength: 305 nm): retention time: 7.85 min; 98.3% purity. MS (M+H): 361.2. Elemental Analysis (C₂₄H₁₂D₉N₃): Calculated: C=79.97; H=5.87; N=11.66. Found: C=79.27; H=5.82; N=11.65.

Example 3

2',6-difluoro-5'-(5-(2-hydroxy-1,1,1,3,3,3-d₆-propan-2-yl)-1H-benzo[d]imidazol-1-yl)biphenyl-2-carbonitrile (Compound 108)

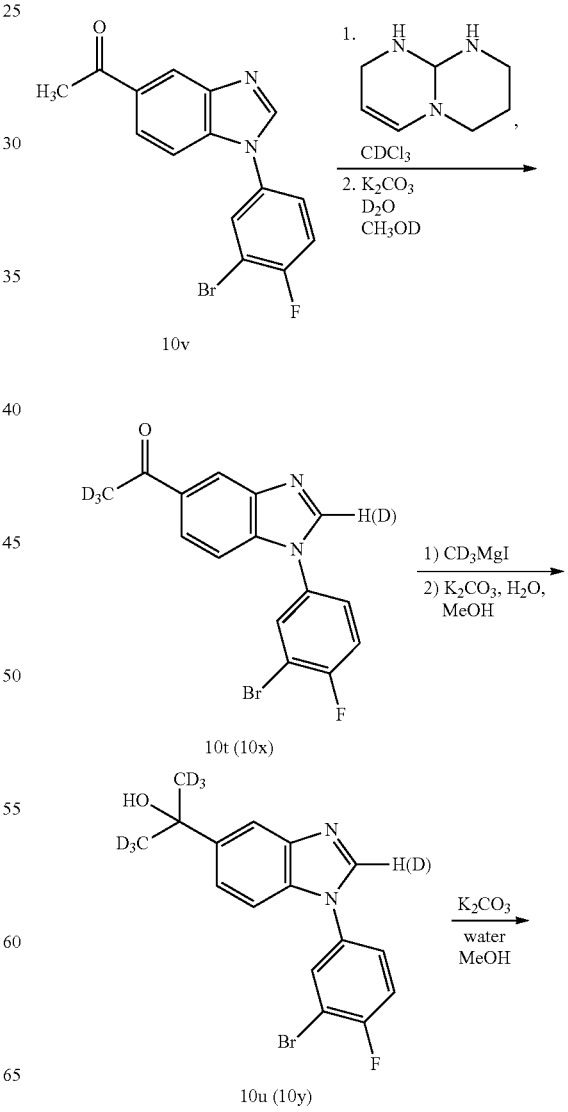

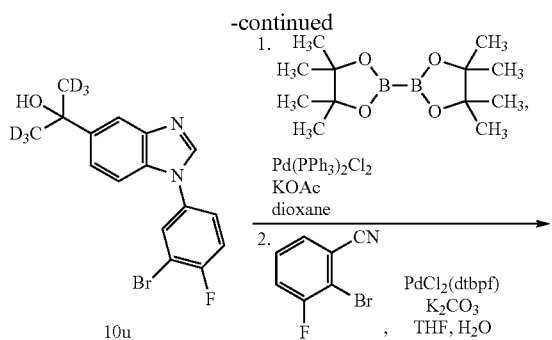

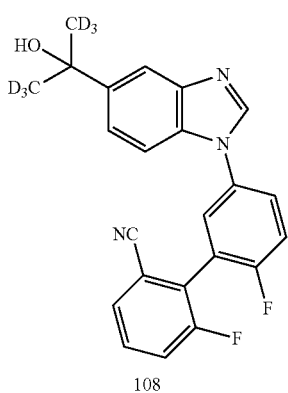

108

Step 1. 1-(1-(3-Bromo-4-fluorophenyl)-1H-benzo[d]imidazol-5-yl)-2,2,2-d₃-ethanone (10t): 10v (3 g, 9 mmol, prepared as described in Scheme 18) was mixed with 2,3,4,6,7,8-hexahydro-1H-pyrimido[1,2-a]pyrimidine (70 mg) in CDCl₃ (Cambridge Isotopes, 99.8 atom % D; 50 mL) and the cloudy mixture was stirred at room temperature for 24 hours, then heated at 60° C. for 3 hours. This material was passed through a short silica gel plug to recover approximately 2.8 g of material. This exchange process was repeated two more times under the conditions described above. ¹H NMR showed approximately 5-10% proton was still present on the α-carbon. The material was then treated with K₂CO₃ (1 g) in CH₃OD (Aldrich, 99.5 atom % D; 30 mL) and D₂O (Cambridge Isotopes, 99 atom % D; 30 mL). The mixture was still cloudy so THF (50 mL) was added. After heating overnight at 70° C., NMR showed about 2% proton still present plus approximately 50% deuteration on the imidazole ring. The mixture was concentrated to remove the volatiles and the residue was extracted with EtOAc (3×100 mL). The combined organic phases were dried (Na₂SO₄) and concentrated. This H/D exchange was performed once more to afford less than 1% proton remaining on the α-carbon by NMR. Concentration to dryness afforded about 2.8 g of 10t with approximately 50% D on the imidazole ring (10x).

Step 2. 2-(1-(3-Bromo-4-fluorophenyl)-1H-benzo[d]imidazol-5-yl)-1,1,1,3,3,3,-d₆-propan-2-ol (10u) 10t (2.85 g, 8.5 mmol, approximately 50% D on imidazole ring) was suspended in THF (30 mL) and cooled in an ice water bath. CD₃MgI (Aldrich, 99+ atom % D; 1M in ether, 11 mL) was slowly added. The mixture was stirred cold for 2 hours then aqueous ammonium chloride (20 mL) was added to quench the reaction. After extraction with EtOAc (2×50 mL), the combined organic phases were dried (Na₂SO₄) and concentrated. The crude product was purified on an Analogix automated chromatography system eluting with 0-50% EtOAc/heptanes to give 2.5 g (85%) of 10u with approximately 50% D on the imidazole ring (10y).

The 10u/10y mix (2 g) was heated overnight at 60-70° C. in water (30 mL)/MeOH (30 mL) in the presence of K₂CO₃ (1 g). The cooled reaction was extracted with EtOAc (2×100 mL) and the combined organic phases were dried (Na₂SO₄) and concentrated to give 1.8 g (90%) of 10u.

Step 3. 2',6-Difluoro-5'-(5-(2-hydroxy-1,1,1,3,3,3-d₆-propan-2-yl)-1H-benzo[d]imidazol-1-yl)biphenyl-2-carbonitrile (108): A mixture of 10u (1.7 g, 4.78 mmol), bis(pinacolato)diboron (1.47 g, 5.8 mmol) and KOAc (1.18 g, 12.0 mmol) in dioxane (30 mL) was purged with nitrogen for 5 minutes. Bis(triphenylphosphine)palladium(II)-dichloride (270 mg, 0.38 mmol) was added and the mixture was heated at 120° C. overnight. The mixture was diluted with EtOAc (200 mL) and the solution was washed with water (2×30 mL) and brine, then dried (Na₂SO₄). After concentrating to dryness the material was dissolved in MeOH (30 mL) and concentrated to dryness again. The concentration step from MeOH was repeated a total of five times until about 2.1 g of a tan colored solid was obtained. This intermediate (2.1 g) was stirred in THF (20 mL) and water (10 mL) and was treated with 3-fluoro-2-bromo-1-cyanobenzene (1.2 g, 6 mmol) and K₂CO₃ (1.5 g, 10.8 mmol). The mixture was purged with nitrogen for five minutes, then bis(di-t-butylphosphine) ferrocene palladium(II) dichloride (130 mg, 0.2 mmol) was added. The solution was heated at 60° C. overnight. The cooled mixture was diluted with EtOAc (120 mL) and washed with water (30 mL). The organic phase was dried (Na₂SO₄) and concentrated. The crude product was purified on an Analogix automated chromatography system eluting with 0-3% MeOH/CH₂Cl₂. The partially purified mixture was further purified on a reverse-phase C18 column eluting with 0-50% acetonitrile/water. The purest fractions were collected and concentrated to remove acetonitrile and the solid was isolated by filtration. This solid was passed through a short silica gel column eluting with 3% MeOH/CH₂Cl₂ to give 320 mg (17%) of 108 with 99.8% purity. ¹H-NMR (300 MHz, CDCl₃): δ 1.89 (s, 1H), 7.42-7.44 (m, 0.19H), 7.45-7.47 (m, 0.65H), 7.47-7.50 (m, 0.76H), 7.51 (app d, J=1.46, 0.33H), 7.53-7.67 (m, 6H), 7.99 (dd, J=0.7, 1.7, 1H), 8.12 (s, 1H). ¹³C-NMR (75 MHz, CDCl₃): δ 109.95, 116.31, 117.79, 118.11, 120.75, 121.05, 121.32, 127.03, 127.15, 127.38, 129.32, 129.37, 131.15, 131.27, 132.53, 142.47, 143.92, 144.65, 158.05, 161.41. HPLC (method: Waters Atlantis T3 2.1 column 2.1×50 mm 3 μm—gradient method 5-95% ACN+0.1% formic acid in 14 min with 4 min hold at 95% ACN+0.1% formic acid; wavelength: 305 nm): retention time: 5.85 min; 99.8% purity. MS (M+H): 396.3. Elemental Analysis (C₂₃H₁₁D₆F₂N₃O): Calculated: C=69.87; H=4.33; F=9.61; N=10.63. Found: C=79.27; H=4.05; F=9.63; N=10.53.

Example 4

5'-(5-tert-Butyl-d₉-1H-benzo[d]imidazol-1-yl)-2',6-difluorobiphenyl-2-carbonitrile (Compound 109)

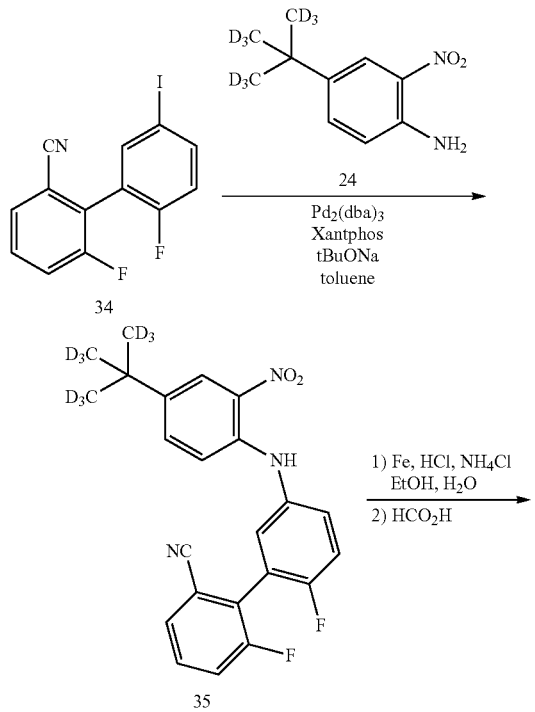

Step 1. 5'-(4-t-Butyl-d₉-2-nitrophenylamino)-2',6-difluorobiphenyl-2-carbonitrile (35): A mixture of 24 (1.18 g, 6 mmol), 34 (1.8 g, 5.2 mmol, prepared as described in Scheme 19), Xantphos (226 mg, 0.39 mmol) and t-BuONa (890 mg, 9 mmol) in toluene (20 mL) was added to a sealed tube. The mixture was purged with nitrogen for 5 minutes then tris(dibenzylideneacetone)dipalladium(0) (Pd₂(dba)₃, 120 mg, 0.13 mmol) was added. The tube was sealed and heated at 130° C. for 6.5 hours then stirred at room temperature overnight. The mixture was diluted with EtOAc (60 mL) and passed through a pad of Celite. The filtrate was concentrated under vacuum. The crude product was purified on an Analogix automated chromatography system eluting with 0-20% EtOAc/heptanes to give 1.5 g (70% yield, 90% purity) of 35 as an orange solid.

Step 2. 5'-(5-tert-Butyl-d₉-1H-benzo[d]imidazol-1-yl)-2',6-difluorobiphenyl-2-carbonitrile (Compound 109): To iron powder (1.2 g, 21 mmol) in EtOH (20 mL) was added HCl (12N, 0.3 mL) and the mixture was stirred for 1 hour at 50° C. Aqueous ammonium chloride solution (25% w/v, 10 mL) was added followed by a solution of 35 (1.5 g, 3.6 mmol) in EtOH (10 mL). The mixture was heated at 60-70° C. for 5 hours. The mixture was passed through a pad of Celite, washing with EtOAc (30 mL), and the filtrate was concentrated to dryness. Formic acid (20 mL) was added to the residue and the mixture was heated at 80° C. for 2 hours. The solution was concentrated, then EtOAc (200 mL) was added. The organic layer was washed with water, aqueous saturated NaHCO₃, and brine. The organic layer was dried (Na₂SO₄) and concentrated to afford 1.4 g of 109 with 80% purity. This material was further purified on an Analogix automated chromatography system eluting with 0-40% EtOAc/heptanes to afford 684 mg (48%) of 109 as a cream colored solid with 99.6% purity. $^{1}$H-NMR (300 MHz, CDCl₃): δ 7.41-7.52 (m, 3H), 7.52-7.69 (m, 5H), 7.89 (app dd, J=0.5, 2.0, 1H), 8.10 (s, 1H). $^{13}$C-NMR (75 MHz, CDCl₃): δ 109.64, 114.84, 114.92, 116.66, 116.72, 116.94, 117.76, 118.06, 120.75, 120.98, 121.05, 121.22, 122.23, 125.69, 125.94, 126.93, 127.05, 127.24, 127.27, 129.32, 129.38, 131.13, 131.25, 131.63, 132.89, 132.94, 142.09, 144.08, 146.61, 157.12, 158.08, 160.46, 161.43. HPLC (method: Waters Atlantis T3 2.1 column 2.1×50 mm 3 μm—gradient method 5-95% ACN+0.1% formic acid in 14 min with 4 min hold at 95% ACN+0.1% formic acid; wavelength: 305 nm): retention time: 8.14 min; 99.6% purity. MS (M+H): 397.2. Elemental Analysis (C₂₄H₁₀D₉F₂N₃): Calculated: C=72.71, H=4.83, F=9.58, N=10.60. Found: C=72.54, H=4.81, F=9.47, N=10.48.

Example 5

1-(5'-fluoro-2'-methoxy-d₃-biphenyl-3-yl)-5-trifluoromethyl-1H-benzo[d]imidazole (Compound 100)

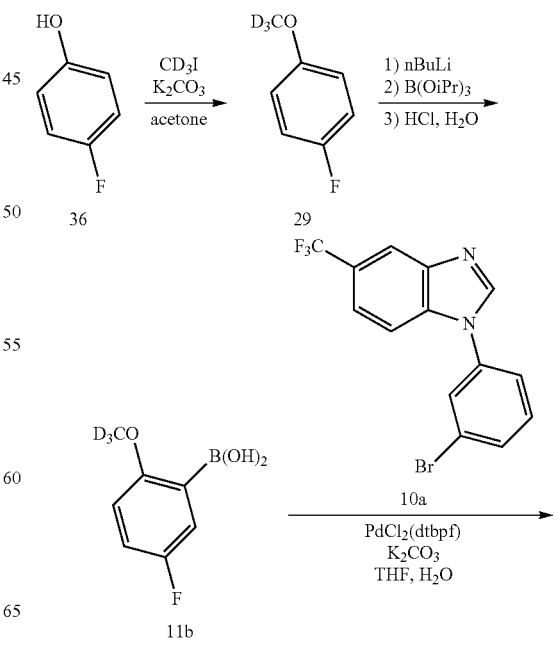

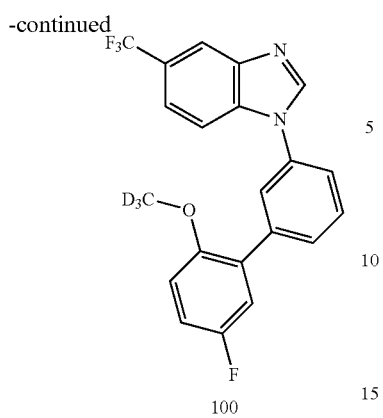

100

Step 1. 1-Fluoro-4-methoxy-d₃-benzene (29): Compound 36 (9 g, 80 mmol) was mixed with iodomethane-d₃ (Cambridge Isotopes, 99.5 atom % D; 13.3 g, 90 mmol) and K₂CO₃ (13.8 g, 100 mmol) in acetone (100 mL). The reaction was sealed and stirred at room temperature for 1 day. The mixture was filtered through a pad of Celite and concentrated. The crude product was purified on a silica gel column eluting with 1:5 MTBE/heptanes to give 2.5 g (25%) of volatile 29.

Step 2. 5-Fluoro-2-methoxy-d₃-phenylboronic acid (11b): 29 (2.5 g, 19 mmol) was dissolved in THF (20 mL) and cooled to −60° C. nBuLi (2.5M in hexane, 8.4 mL, 21 mmol) was added. After stirring for 3 hours the mixture was cooled to −78° C. and B(OiPr)₃ (5.5 g, 30 mmol) was added. The mixture was warmed to room temperature over 1 hour, then stirred overnight. HCl (1N, 25 mL) was added and the aqueous phase was extracted with EtOAc (3×40 mL). The organic phase was partially concentrated to about 50 mL, then extracted with NaOH (3×20 mL) solution. The combined basic aqueous layer was washed with EtOAc (2×10 mL). Concentrated HCl was added to the aqueous layer to bring the pH to 3-4. The mixture was filtered to provide about 1.2 g of yellow solid. The solid was triturated with CH₂Cl₂ (4 mL)/ heptanes (20 mL) to afford 1 g (30%) of 11b.

Step 3. 1-(5'-Fluoro-2'-methoxy-d₃-biphenyl-3-yl)-5-(trifluoromethyl)-1H-benzo[d]imidazole (Compound 100): 10a (1.0 g, 3.0 mmol, prepared as described in Scheme 20) was mixed with 11b (0.62 g, 3.6 mmol) and K₂CO₃ (1.04 g, 7.5 mmol) in THF (20 mL) and water (10 mL). The mixture was purged with nitrogen for 5 minutes. Bis(di-t-butylphosphine) ferrocenepalladium(II) dichloride (100 mg, 0.15 mmol) was added and the reaction was heated at 60-70° C. overnight. The mixture was diluted with EtOAc and the organic solution was washed with water and brine, then dried (Na₂SO₄) and concentrated. The crude material was purified on an Analogix automated chromatography system eluting with 0-50% EtOAc/heptanes to give 1.05 g (89%) of 100. The product was further purified by crystallization from MTBE/heptanes to give 720 mg of 100 with greater than 99% purity. $^1$H-NMR (300 MHz, CDCl₃): δ 6.95 (ddd, J=0.4, 4.4, 8.9, 1H), 7.03-7.10 (m, 1H), 7.12 (ddd, J=0.4, 3.2, 8.6, 1H), 7.48 (td, J=2.2, 6.9, 1H), 7.57-7.72 (m, 4H), 7.72-7.77 (m, 1H), 8.17-8.20 (m, 1H), 8.26 (s, 1H). $^{13}$C-NMR (75 MHz, CDCl₃): δ 111.09, 112.31, 112.42, 115.24, 115.54, 117.13, 117.45, 118.43, 118.48, 120.60, 120.65, 122.83, 125.33, 129.37, 130.08, 135.39, 143.56, 144.07, 158.72. HPLC (method: Waters Atlantis T3 2.1 column 2.1×50 mm 3 μm—gradient method 5-95% ACN+0.1% formic acid in 14 min with 4 min hold at 95% ACN+0.1% formic acid; wavelength: 305 nm): retention time: 9.56 min; 99.2% purity. MS (M+H): 390.3. Elemental Analysis (C₂₁H₁₁D₃F₄N₂O): Calculated: C=64.78; H=3.62; N=7.20; F=19.52. Found: C=64.57; H=3.43; N=7.05; F=19.27.

Example 6

3'-(5-tert-butyl-1H-benzo[d]imidazol-1-yl)biphenyl-2-carbonitrile (Compound 110)

Scheme 17. Preparation of Compound 110.

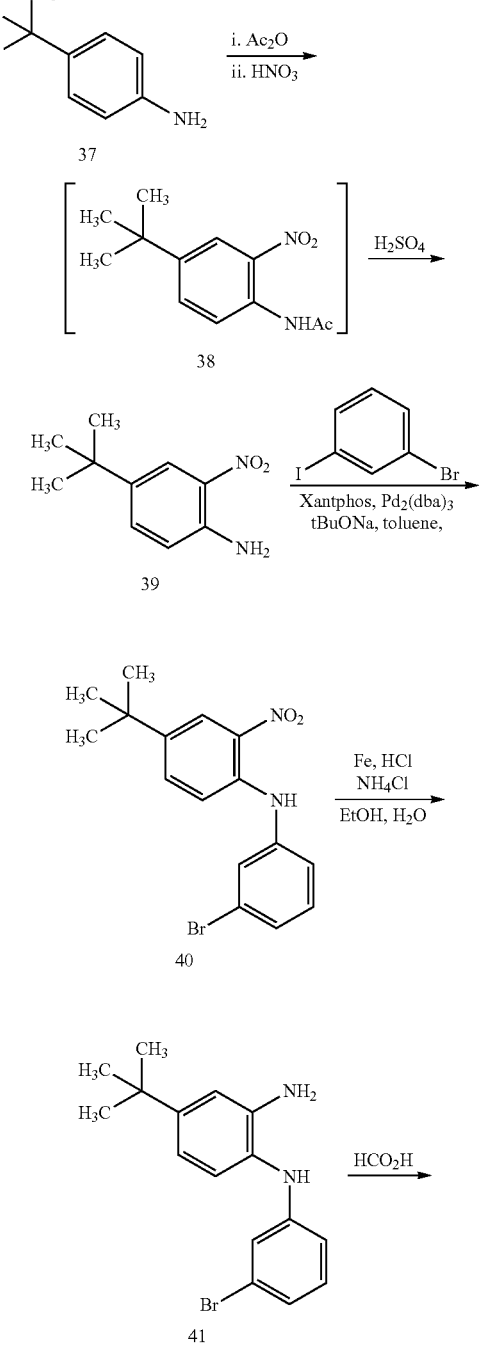

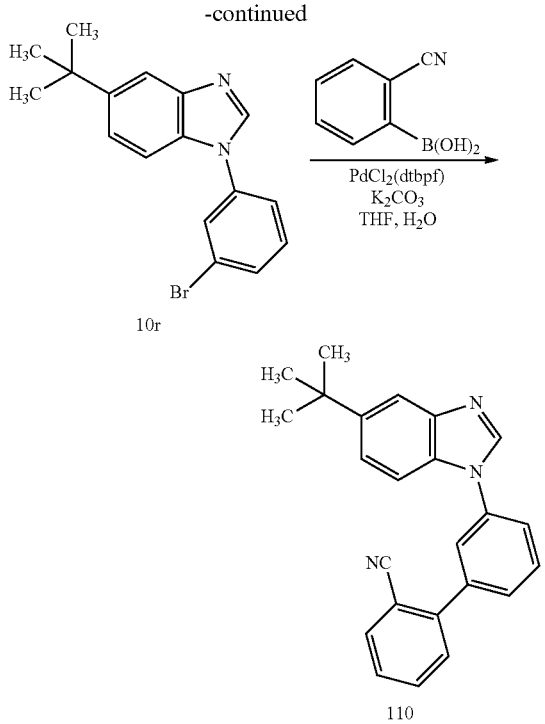

Step 1. 4-t-Butyl-2-nitroaniline (39): A solution of 4-t-butylaniline (25 g, 167 mmol) in acetic anhydride (250 mL) was cooled in an ice water bath. Nitric acid (70%, 20 mL) was added drop-wise (at less than 10° C., internal temperature). The solution was allowed to warm to room temperature and was stirred overnight. The mixture was poured into ice water (600 mL) and the solid was collected to give about 41 g (wet) of crude 38. Concentrated H₂SO₄ (100 mL) was added to water (50 mL), then crude 38 was added to the still hot solution. The reaction was heated at 100° C. for 1 hour then stirred at room temperature overnight. The mixture was poured into ice water (600 mL) and the solid was filtered, washed with water, and retained. The filtrate was extracted with EtOAc (200 mL) and the EtOAc solution was washed with NaHCO₃ (2×50 mL). This organic phase was combined with the solid which had been collected and the mixture was dry-loaded onto a silica gel column eluting with 1:9-1:5 EtOAc/heptanes to give 21 g (63%) of 39.

Step 2. N-(3-Bromophenyl)-4-t-butyl-2-nitroaniline (40): To a sealed tube was added 39 (6 g, 30 mmol), 3-bromoiodobenzene (11.2 g, 40 mmol), Xantphos (0.52 g, 0.9 mmol), sodium tert-butoxide (4.4 g, 46 mmol) and toluene (90 mL). The mixture was purged with nitrogen for 5 minutes then tris(dibenzylideneacetone)dipalladium(0) (Pd₂(dba)₃, 0.28 g, 0.3 mmol) was added. The tube was sealed and heated at 100-110° C. for 5 hours. The reaction was cooled and combined with a 2 g scale front run. The mixture was filtered through a pad of Celite, washing with EtOAc (100 mL). The filtrate was adsorbed onto silica gel and dry-loaded onto a silica gel column eluting with 0-1:6 EtOAc/heptanes to give 13 g (92%) of 40 as a red solid.

Step 3. 1-(3-Bromophenyl)-5-t-butyl-1H-benzo[d]imidazole (10r): A three-necked flask equipped with a mechanical stirrer, nitrogen inlet, and thermowell was charged with iron powder (10.5 g, 186 mmol) and EtOH (80 mL). HCl (12 N, 1.6 mL) was added and the mixture was stirred for 1 hour at 50° C. Aqueous ammonium chloride solution (25% w/v, 40 mL) was added followed by the portion-wise addition of 40 (13 g, 37.2 mmol). The mixture was heated at 60-70° C. for 5 hours. The dark mixture was filtered through a pad of Celite washing with EtOAc (200 mL), and the filtrate was concentrated to dryness. Formic acid (40 mL) was added and the reaction was heated at 80° C. for 2 hours. LCMS showed complete cyclization. The mixture was cooled and poured into ice water (400 mL). The solid was collected, washed with water (200 mL) followed by heptanes (100 mL), then dried in a vacuum oven at 50° C. overnight to afford 12 g (98%) of 10r. The solid was dissolved in EtOAc (150 mL) and the solution was concentrated under vacuum until a white solid began to appear. The mixture was then allowed to stand overnight. The white solid was collected to afford 5 g of 10r with 99.7% purity.

Step 4. 3'-(5-t-Butyl-1H-benzo[d]imidazol-1-yl)biphenyl-2-carbonitrile (Compound 110): A mixture of 10r (1.5 g, 4.5 mmol), 2-cyanobenzeneboronic acid (1.02 g, 6.9 mmol) and K₂CO₃ (1.27 g, 9.2 mmol) in THF (20 mL) and water (10 mL) was purged with nitrogen for 5 minutes. Bis(di-t-butylphosphine)ferrocenepalladium(II) dichloride (0.15 g, 0.23 mmol) was added and the mixture was heated at 50° C. for 24 hours. The cooled reaction mixture was diluted with water (20 mL) and extracted with EtOAc (3×50 mL). The combined organic phases were dried (Na₂SO₄) and concentrated. The crude product was purified on an Analogix automated chromatography system eluting with 0-2% MeOH/CH₂Cl₂. Concentration of product fractions gave a sticky semi-solid. This material was further purified on an Analogix reverse-phase C18 column eluting with 0-100% MeOH/water to give 720 mg (46%) of 110. ¹H-NMR (300 MHz, CDCl₃): δ 1.42 (s, 9H), 7.51 (dq, J=1.8, 8.8, 1H), 7.46-7.74 (m, 8H), 7.83 (dd, J=1.1, 7.7, 1H), 7.92 (d, J=1.4, 1H), 8.25 (s, 1H). ¹³C-NMR (75 MHz, CDCl₃): δ 31.78, 34.89, 110.14, 111.41, 116.54, 118.49, 122.39, 123.84, 124.15, 128.32, 128.39, 130.06, 130.64, 133.13, 133.91, 136.75, 140.23, 141.97, 143.87, 146.91. HPLC (method: Waters Atlantis T3 2.1 column 2.1× 50 mm 3 μm—gradient method 5-95% ACN+0.1% formic acid in 14 min with 4 min hold at 95% ACN+0.1% formic acid; wavelength: 305 nm): retention time: 8.58 min; >99% purity. MS (M+H): 352.2. Elemental Analysis (C₂₃H₁₉N₃O): Calculated: C=80.37; H=6.13; N=11.72. Found: C=80.33; H=5.68; N=11.45.

Example 7

2',6-Difluoro-5'-(5-(2-hydroxypropan-2-yl)-1H-benzo[d]imidazol1-yl)biphenyl-2-carbonitrile (Compound 111)

Scheme 18. Preparartion of Compound 111.

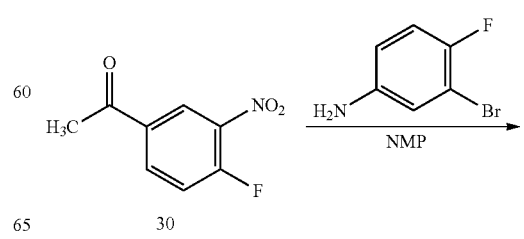

30

-continued

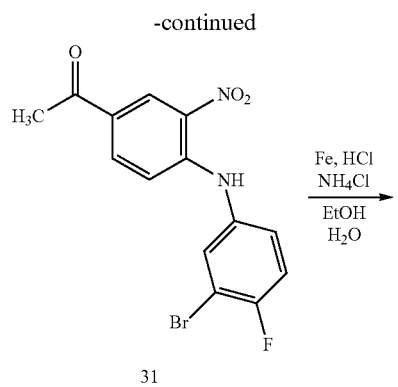
31

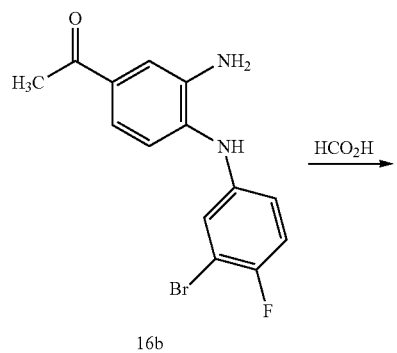
16b

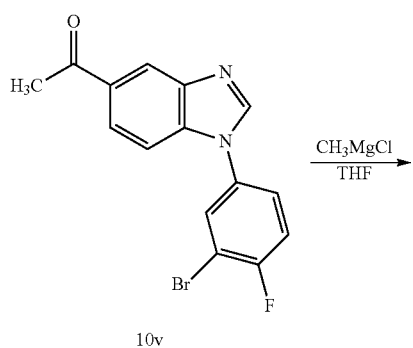
10v

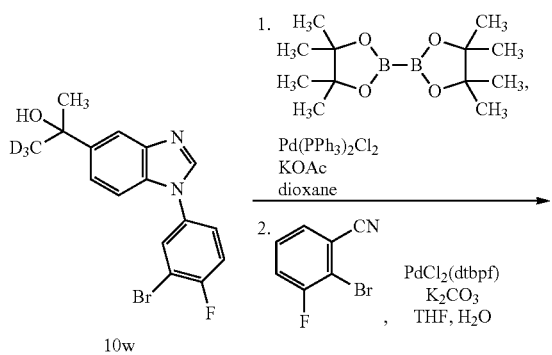
10w

-continued

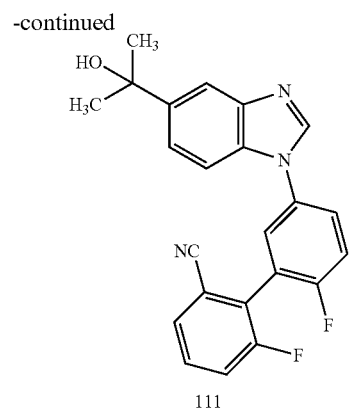
111

Step 1. 1-(4-(3-Bromo-4-fluorophenylamino)-3-nitrophenyl)ethanone (31): 30 (5 g, 27.3 mmol) was mixed with 3-bromo-4-fluoroaniline (8.3 g, 44 mmol) in NMP (20 mL) and heated at 90° C. After 3 days the reaction was cooled and the mixture was poured into ice water (500 mL). The orange solid was filtered, washed with water (200 mL) and then washed with heptanes (100 mL). After drying under vacuum for 6 hours at 50° C., 11.2 g (>100%) of 31 was obtained. The sample contained residual NMP by NMR and was used directly in the next step.

Step 2. 1-(1-(3-Bromo-4-fluorophenyl)-1H-benzo[d]imidazol-5-yl)ethanone (10v): A three-necked flask equipped with a mechanical stirrer, nitrogen inlet, and thermowell was charged with iron powder (7.3 g, 130 mmol) and EtOH (50 mL). HCl (12 N, 1.1 mL) was added and the mixture was stirred for 2 hours at 50° C. Aqueous ammonium chloride solution (25% w/v, 25 mL) was added followed by the portion-wise addition of 31 (9.2 g, 26 mmol). The mixture was heated at 60-70° C. for 5 hours. The dark mixture was combined with a 2 g front run and passed through a pad of Celite, washing with EtOAc (100 mL), and the filtrate was concentrated to dryness to afford crude 16b. Formic acid (40 mL) was added and the mixture was heated at 80° C. for 2 hours. The mixture was cooled and poured into ice water (300 mL). The solid was filtered and washed with water (200 mL), saturated NaHCO$_3$ solution (100 mL), water (200 mL) and heptanes (100 mL). Drying in a vacuum oven at 50° C. overnight provided 7.8 g (85% from 31) of 10v.

Step 3. 2-(1-(3-Bromo-4-fluorophenyl)-1H-benzo[d]imidazol-5-yl)propan-2-ol (10w): 10v (2.4 g, 7.2 mmol) was dissolved in THF (75 mL) and the solution was cooled in an ice water bath. CH$_3$MgCl (3 M in THF, 5 mL) was added and the reaction was stirred at room temperature for 2 hours. Saturated ammonium chloride solution (50 mL) was added to quench the reaction and the mixture was extracted with EtOAc (3×50 mL). The combined organic phases were dried (Na$_2$SO$_4$) and concentrated. The crude product was purified on an Analogix automated chromatography system eluting with 0-5% MeOH/CH$_2$Cl$_2$ to give 1.9 g (75%) of 10w.

Step 4. 2',6-Difluoro-5'-(5-(2-hydroxypropan-2-yl)-1H-benzo[d]imidazol-1-yl)biphenyl-2-carbonitrile (Compound 111): A mixture of 10w (1.52 g, 4.3 mmol), bis(pinacolato)-diboron (1.3 g, 5.2 mmol) and KOAc (1.05 g, 10.75 mmol) in dioxane (30 mL) was purged with nitrogen for 5 minutes. Bis(triphenylphosphine)palladium(II) dichloride (241 mg, 0.34 mmol) was added and the mixture was heated at 100° C. overnight. The mixture was diluted with EtOAc (100 mL) and the organic solution was washed with water (2×30 mL) and then brine, dried (Na$_2$SO$_4$), and concentrated. MeOH (30 mL) was added and the solution was concentrated to dryness again. The concentration step from MeOH was repeated a total of four times until a tan colored solid was obtained. This crude solid was dissolved in THF (20 mL) and water (10 mL). 3-Fluoro-2-bromo-cyanobenzene (1.2 g, 6 mmol) was added, followed by K$_2$CO$_3$ (1.5 g, 10.8 mmol), and the mixture was purged with nitrogen for 5 minutes. Bis(di-t-butylphosphine) ferrocene palladium(II) dichloride (140 mg, 0.22 mmol) was added and the solution was heated at 60° C. overnight. The cooled mixture was diluted with EtOAc (120 mL) and washed with water (30 mL). The organic phase was dried (Na$_2$SO$_4$) and concentrated. The crude product was purified on an Analogix automated chromatography system eluting with 0-3% MeOH/CH$_2$Cl$_2$. The partially purified mixture was further purified on a reverse-phase C18 column eluting with 0-50% acetonitrile/water. The purest fractions were collected and concentrated to remove acetonitrile and the solid was isolated by filtration. This solid was further passed through a silica gel column eluting with 3% MeOH/CH$_2$Cl$_2$ to give 370 mg (22%) of 111. $^1$H-NMR (300 MHz, CDCl$_3$): δ 1.67 (s, 6H), 7.43-7.51 (m, 2H), 7.54-7.68 (m, 6H), 8.00-8.01 (m, 1H), 8.11 (s, 1H). $^{13}$C-NMR (75 MHz, CDCl$_3$): δ 32.14, 72.65, 109.93, 114.81, 114.87, 116.31, 116.63, 116.69, 117.78, 118.10, 120.76, 121.03, 121.05, 121.26, 121.37, 125.59, 125.85, 127.02, 127.14, 127.34, 127.36, 129.32, 129.37, 131.16, 131.28, 132.48, 132.68, 132.73, 142.44, 143.83, 144.79, 157.19, 158.06, 160.54, 161.40. HPLC (method: Waters Atlantis T3 2.1 column 2.1×50 mm 3 μm—gradient method 5-95% ACN+0.1% formic acid in 14 min with 4 min hold at 95% ACN+0.1% formic acid; wavelength: 305 nm): retention time: 5.87 min; 99.7% purity. MS (M+H): 390.3. Elemental Analysis (C$_{23}$H$_{17}$F$_2$N$_3$O): Calculated: C=70.94; H=4.40; N=10.79; F=9.76. Found: C=66.24; H=4.10; N=9.90; F=8.95.

Example 8

5'-(5-tert-butyl-1H-benzo[d]imidazol-1-yl)-2',6-difluorobiphenyl-2-carbonitrile (Compound 112)

Scheme 19. Preparation of Compound 112.

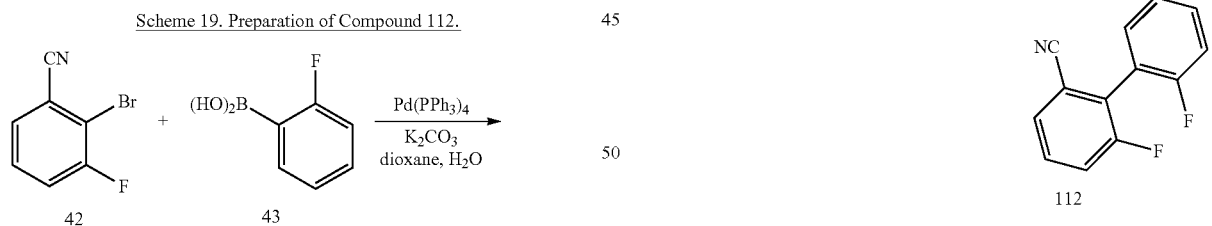

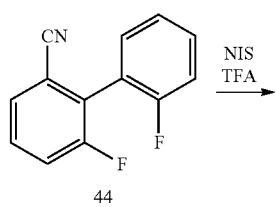

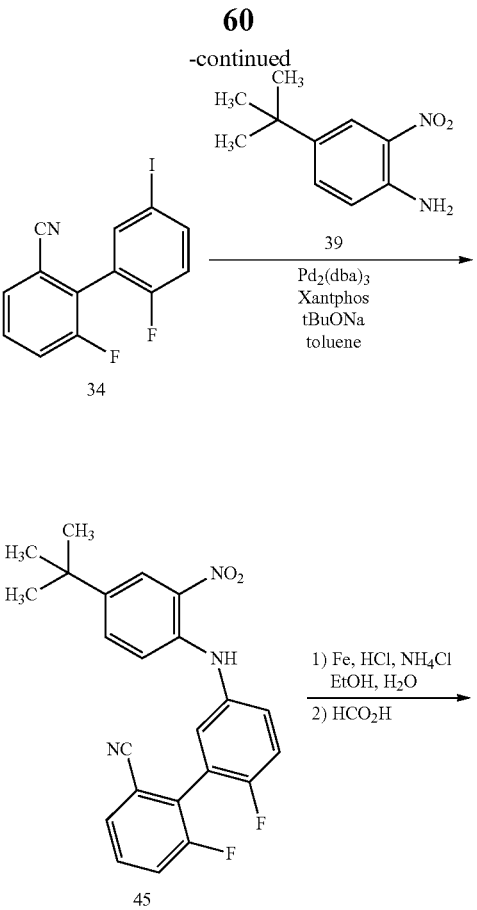

Step 1. 2',6-Difluorobiphenyl-2-carbonitrile (44): 2-Bromo-3-fluorobenzonitrile (10 g, 50 mmol) was mixed with 2-fluorophenylboronic acid (8.75 g, 62.5 mmol) and K$_2$CO$_3$ (22 g, 157 mmol) in dioxane (120 mL) and water (30 mL). The mixture was purged with nitrogen for 10 minutes then tetrakis(triphenylphosphine)palladium (3.5 g, 6 mol %) was added. The reaction was heated at 120° C. for two days. The mixture was cooled and diluted with EtOAc (100 mL). The organic layer was washed with water (10 mL), dried (Na$_2$SO$_4$), and concentrated. The crude product was purified on an Analogix automated chromatography system eluting with 0-20% EtOAc/heptanes to give 8.2 g (76%) of 44 that was contaminated with a small amount of 2-bromo-3-fluorobenzonitrile.

Step 2. 2',6-Difluoro-5'-iodobiphenyl-2-carbonitrile (34): 44 (2.2 g, 10.2 mmol) was dissolved in TFA (20 mL) then NIS (2.52 g, 11.2 mmol) was added. The reaction was stirred at room temperature overnight. This reaction was combined with a 0.5 g front run and concentrated to remove most of the TFA. The residue was dissolved in EtOAc (100 mL) and washed with aqueous saturated NaHCO$_3$ and brine, then dried (Na$_2$SO$_4$) and concentrated. The crude material was purified on an Analogix automated chromatography system eluting with 0-20% EtOAc/heptanes. The product was further purified by crystallization from EtOAc/heptanes to remove most of the residual unreacted 2-bromo-3-fluorobenzonitrile from the previous step. The crystallization afforded about 2 g (45%) of 34.

Step 3. 5'-(4-t-Butyl-2-nitrophenylamino)-2',6-difluorobiphenyl-2-carbonitrile (45): A mixture of 39 (0.8 g, 4.1 mmol), 34 (1.28 g, 3.75 mmol), Xantphos (136 mg, 0.28 mmol) and t-BuONa (620 mg, 6.5 mmol) in toluene (16 mL) was placed in a sealed tube. The mixture was purged with nitrogen for 5 minutes then tris(dibenzylideneacetone)dipalladium(0) (Pd$_2$(dba)$_3$, 86 mg, 0.094 mmol) was added. The tube was sealed and heated at 130° C. for 4 hours. The cooled mixture was diluted with EtOAc (60 mL) and passed through a pad of Celite, washing with EtOAc. The filtrate was concentrated and the crude product purified on an Analogix automated chromatography system eluting with 0-20% EtOAc/heptanes to give 0.82 g (50%) of 45 (85% purity) as an orange solid. The optimal reaction time was later determined to be approximately 6-7 hr.

Step 4. 5'-(5-tert-Butyl-1H-benzo[d]imidazol-1-yl)-2',6-difluorobiphenyl-2-carbonitrile (Compound 112): To iron powder (0.5 g, 9 mmol) in EtOH (10 mL) was added HCl (12 N, 0.1 mL). The mixture was stirred for 1 hour at 50° C. Aqueous ammonium chloride solution (25% w/v, 5 mL) was added followed by a solution of 45 (0.8 g, 2 mmol) in EtOH (5 mL) and the mixture was heated at 60-70° C. for 3 hours. The mixture was passed through a pad of Celite washing with EtOAc (30 mL). The filtrate was concentrated to dryness. Formic acid (10 mL) was added to the residue and the reaction mixture was heated at 80° C. for 2 hours. The solution was concentrated and diluted with EtOAc (50 mL). The organic layer was washed with water, aqueous saturated NaHCO$_3$, and brine, then dried (Na$_2$SO$_4$). After concentration the crude material was purified on an Analogix automated chromatography system eluting with 0-40% EtOAc/heptanes to afford 350 mg (50%) of 112 with 99.9% purity. $^1$H-NMR (300 MHz, CDCl$_3$): δ 1.41 (s, 9H), 7.42-7.51 (m, 3H), 7.53-7.68 (m, 5H), 7.90 (d, J=1.3, 1H), 8.10 (s, 1H). $^{13}$C-NMR (75 MHz, CDCl$_3$): δ 31.78, 34.85, 109.62, 114.91, 116.64, 116.70, 116.93, 117.74, 118.06, 120.73, 120.97, 121.04, 121.20, 122.22, 126.91, 127.03, 127.23, 127.26, 129.31, 129.36, 131.12, 131.23, 131.63, 132.87, 132.92, 142.09, 144.06, 146.58, 157.10, 158.07, 160.45, 161.41. HPLC (method: Waters Atlantis T3 2.1 column 2.1×50 mm 3 μm—gradient method 5-95% ACN+0.1% formic acid in 14 min with 4 min hold at 95% ACN+0.1% formic acid; wavelength: 305 nm): retention time: 8.17 min; 99.9% purity. MS (M+H): 388.2.

Elemental Analysis (C$_{23}$H$_{11}$D$_6$F$_2$N$_3$O): Calculated: C=74.4; H=4.94; N=10.85; F=9.81. Found: C=74.2; H=4.81; N=10.68; F=9.83.

Example 9

1-(3-Bromophenyl)-5-tert-butyl-1H-benzo[d]imidazole (10a)

Scheme 20. Preparation of Intermediate (10a):

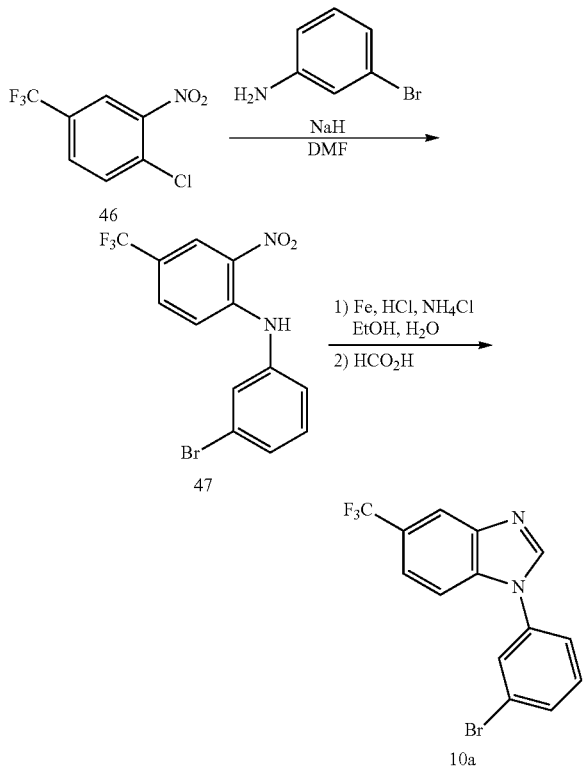

Step 1. N-(3-Bromophenyl)-2-nitro-4-(trifluoromethyl)aniline (47): 46 (5 g, 22.2 mmol) and 3-bromoaniline (4.2 g, 24.4 mmol) were dissolved in DMF (25 mL). NaH (60%, 1.68 g, 42 mmol) was added slowly portion-wise over 30 minutes. An exotherm was observed. The reaction was stirred at room temperature overnight, then poured into ice water (50 mL). The mixture was extracted with EtOAc (3×100 mL) and the combined organic solution was dried (Na$_2$SO$_4$) and concentrated. The product was purified on a silica gel column eluting with 1:12 EtOAc/heptanes to give 6.7 g (84%) of 47.

Step 2. 1-(3-Bromophenyl)-5-(trifluoromethyl)-1H-benzo[d]imidazole (10a): To iron powder (5 g, 88.5 mmol) in EtOH (50 mL) was added HCl (12 N, 0.73 mL) and the mixture was stirred for 1 hour at 50° C. Aqueous ammonium chloride solution (25% w/v, 30 mL) was added. 47 (6.4 g, 17.7 mmol) was added as a solution in MTBE/EtOH (30 mL) and the mixture was heated at 60-70° C. for 5 hours. The dark mixture was passed through a pad of Celite, washing with EtOAc (100 mL). The filtrate was concentrated to dryness and formic acid (40 mL) was added to the residue. The reaction mixture was heated at 80° C. for 2 hours. LCMS indicated the cyclization was complete. The reaction mixture was concentrated and the residue was diluted with EtOAc (200 mL). The organic solution was washed with water, aqueous saturated NaHCO$_3$, and brine. The organic layer was dried (Na$_2$SO$_4$), and concentrated. The crude product was purified on silica gel eluting with 1:3 EtOAc/heptanes to give 4.8 g (80%, 2 steps) of 10a. A portion of 10a (2.75 g) was further purified by trituration with EtOAc/heptanes (1:4, 5 mL) to give 1.6 g of 10a as a white solid with >99% purity. MS (M+H): 342.9.

Example 10

Evaluation of Metabolic Stability in Human Liver Microsomes

Human liver microsomes (20 mg/mL) were available from Xenotech, LLC (Lenexa, Kans.). β-nicotinamide adenine dinucleotide phosphate, reduced form (NADPH), magnesium chloride (MgCl$_2$), and dimethyl sulfoxide (DMSO) are available from Sigma-Aldrich.

7.5 mM stock solutions of test compound 102 as well as of NS11394 were prepared in DMSO. The 7.5 mM stock solutions were diluted to 12.5 in acetonitrile (ACN). The 20 mg/mL human liver microsomes were diluted to 2.5 mg/mL in 0.1 M potassium phosphate buffer, pH 7.4, containing 3 mM MgCl$_2$. The diluted microsomes were added to wells of a 96-well deep-well polypropylene plate in triplicate. A 10 mL aliquot of the 12.5 test compound 102 was added to the microsomes and the mixture was pre-warmed for 10 minutes. Reactions were initiated by addition of pre-warmed NADPH solution. The final reaction volume was 0.5 mL and contained 2.0 mg/mL human liver microsomes, 0.25 test compound, and 2 mM NADPH in 0.1 M potassium phosphate buffer, pH 7.4, and 3 mM MgCl$_2$. The reaction mixtures were incubated at 37° C., and 50 mL aliquots were removed at 0, 5, 10, 20, and 30 minutes and added to shallow-well 96-well plates which contain 50 mL of ice-cold ACN with internal standard to stop the reactions. The plates were stored at 4° C. for 20 minutes after which 100 mL of water was added to the wells of the plate before centrifugation to pellet precipitated proteins. Supernatants were transferred to another 96-well plate and analyzed for amounts of parent remaining by LC-MS/MS using an AB SCIEX QTRAP® 5500. Testing was done in triplicate.

The in vitro $t_{1/2}$s for test compounds were calculated from the slopes of the linear regression of % parent remaining (ln) vs incubation time relationship:

in vitro $t_{1/2}$=0.693/k k=−[slope of linear regression of % parent remaining (ln) vs incubation time].

Data analysis was performed using Microsoft Excel Software.

The results of the Human Liver Microsome study are shown in the table below and in the FIGURE. The testing was done in triplicate and the values shown in the table reflect the average of 3 experiments. In the Table and the FIGURE, "% Parent remaining" refers to the percentage of starting material remaining at the specified time point.

TABLE 3

Stability of Compound 102 in Human Liver Microsomes.

| Compound | % Parent Remaining (30 min) Ave ± SD | $t_{1/2}$ (min) Ave ± SD |
|---|---|---|
| NS11394 | 77 ± 3.7 | 95 ± 35 |
| Compound 102 | 101 ± 8.7 | NC* |

*$t_{1/2}$ not calculable due to <20% metabolism in HLM and flat % parent remaining vs time profiles Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

What is claimed is:

1. The compound of 102:

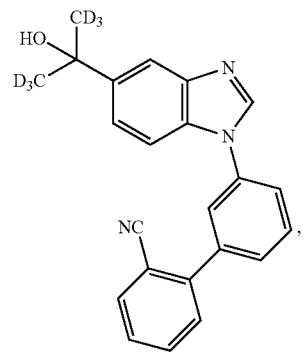

or a pharmaceutically acceptable salt thereof, wherein any atom not designated as deuterium is present at its natural isotopic abundance.

2. A pyrogen-free pharmaceutical composition comprising a compound of claim 1 or a pharmaceutically acceptable salt of said compound; and a pharmaceutically acceptable carrier.

3. The composition of claim 2 additionally comprising a therapeutic agent useful in the treatment of a disease or condition selected from anxiety, convulsions, skeletal muscle spasm, spasticity, athetosis, epilepsy, stiff-person syndrome, and pain.

4. A method of treating a disease or condition selected from anxiety, convulsions, skeletal muscle spasm, spasticity, athetosis, epilepsy, stiff-person syndrome, and pain, in a subject comprising the step of administering to the subject an effective amount of a composition of claim 2.

5. The method of claim 4, wherein the disease or condition is anxiety or convulsions.

* * * * *